(12) United States Patent
Lee et al.

(10) Patent No.: US 6,620,831 B2
(45) Date of Patent: Sep. 16, 2003

(54) INDAZOLES SUBSTITUTED WITH 1,1-DIOXOISOTHIAZOLIDINES USEFUL AS INHIBITORS OF CELL PROLIFERATION

(75) Inventors: Jin-Ho Lee, Taejon (KR); Chang-Yong Hong, Taejon (KR); Tae-Sik Park, Taejon (KR); Jong-Hyun Kim, Taejon (KR); Sei-Hyun Choi, Taejon (KR); Sook-Kyung Yoon, Taejon (KR); Hyun-Ho Chung, Taejon (KR); Shin-Wu Jeong, Taejon (KR); Kwang-Yeon Hwang, Taejon (KR); Dong-Kyu Shin, Taejon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/275,176

(22) PCT Filed: May 10, 2001

(86) PCT No.: PCT/KR01/00759

§ 371 (c)(1),
(2), (4) Date: Nov. 4, 2002

(87) PCT Pub. No.: WO01/85726

PCT Pub. Date: Nov. 15, 2001

(65) Prior Publication Data

US 2003/0149034 A1 Aug. 7, 2003

(30) Foreign Application Priority Data

May 10, 2000 (KR) .......................... 2000/24861

(51) Int. Cl.$^7$ ..................... C07D 417/14; A61K 31/425
(52) U.S. Cl. ..................... 514/372; 548/214; 548/181; 544/133; 544/367; 546/199; 546/271.1
(58) Field of Search .............................. 548/214, 181; 514/372; 544/133, 367; 546/271.1, 191

(56) References Cited

FOREIGN PATENT DOCUMENTS

| EP | 0 241 003 A2 | 10/1987 |
|---|---|---|
| EP | 0 336 061 A2 | 10/1989 |
| WO | WO 97/20842 A | 6/1997 |
| WO | WO 98/33798 A2 | 8/1998 |
| WO | WO 98/49146 A2 | 11/1998 |
| WO | WO 99/21845 A2 | 5/1999 |

*Primary Examiner*—Robert Gerstl
(74) *Attorney, Agent, or Firm*—Birch, Stewart, Kolasch & Birch, LLP

(57) ABSTRACT

The present invention relates to an indazole derivative, pharmaceutically acceptable salt, solvated product and isomer thereof substituted with 1,1-dioxoisothiazolidine which are useful as inhibitors for Cyclin Dependent Kinase(CDK). The present invention also relates to an agent for inhibiting and treating diseases involving cell proliferation, e.g., cancer, inflammation, restenosis, angiogenesis, etc. which comprises the compound of formula (1) as an active ingredient together with a pharmaceutically acceptable carrier.

8 Claims, No Drawings

INDAZOLES SUBSTITUTED WITH 1,1-DIOXOISOTHIAZOLIDINE USEFUL AS INHIBITORS OF CELL PROLIFERATION

TECHNICAL FIELD

The present invention relates to a novel indazole derivative represented by the following formula (1):

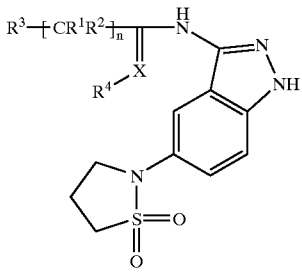

in which n represents 0, 1, 2 or 3,

X represents oxygen, sulfur or nitrogen atom, $R^1$ and $R^2$ each independently represent hydrogen, amino, hydroxy, lower alkyl or cycloalkyl, or together form cycloalkyl, $R^3$ represents hydrogen; lower alkyl; phenyl or naphthyl which may be unsubstituted or substituted with one to three substituents selected from the group consisting of hydroxy, halogen, nitro, amide, ester, carboxy, cyano, amidinyl, —O—$R^5$, —$NR^6R^7$, phenyl, alkylsulfanyl, $R^8$—$SO_2$—, lower alkyl, lower alkyl substituted with $R^9$, pyridinyl, piperidinyl, morpholinyl, piperazinyl, thienyl and furyl; aromatic and bicyclic aromatic compounds bearing at least one heteroatom selected from nitrogen, oxygen or sulfur atom; $C_{3-7}$-cycloalkyl bearing at least one heteroatom selected from nitrogen, oxygen or sulfur atom; piperazinyl, imidazolyl, morpholinyl or piperidinyl which may be unsubstituted or substituted with one or two substituents selected from the group consisting of lower alkyl, phenyl, phenyl substituted with halogen, phenyl substituted with alkoxy, phenyl substituted with alkylcarbonyl, biphenyl and naphthyl; thiazole which may be unsubstituted or substituted with amino, mono- or di-lower alkylamino, alkylcarbonylamino, benzylamino, benzyloxycarbonylamino, benzyloxybenzylamino or alkoxycarbonylamino; benzodioxol; isoquinoline; indolyl; or benzimidazole wherein $R^5$ represents phenyl, benzyl, lower alkyl, alkoxyalkyl, alkoxyalkoxylalkyl, alkoxyalkoxyalkoxyalkyl, aminoalkyl or mono- or di-alkylaminoalkyl, $R^6$ and $R^7$ are identical or different from each other and represent hydrogen, lower alkyl, oxygen or benzyl, or joined to form a ring, and $R^8$ and $R^9$ represent each independently lower alkyl, amino, morpholinyl, piperazinyl, N-alkylpiperazinyl or imidazole, and $R^4$ represents nothing when X is oxygen or sulfur atom, but represents hydroxy or alkoxy when X is nitrogen atom, pharmaceutically acceptable salt, solvated product and isomer thereof which are useful as inhibitors for Cyclin Dependent Kinase(hereinafter, refered to as "CDK"), and method for preparing the same.

The present invention also relates to an agent for inhibiting and treating diseases involving cell proliferation such as cancer, inflammation, restenosis and angiogenesis which comprises the compound of formula (1) as an active ingredient together with a pharmaceutical carrier.

BACKGROUND ART

Researches on cell division process in molecular level have been extensively performed from the late 1980's through study of division of frog oocytes, analysis several yeast cell growth or characterization of induced mutants by radiation and study of the tumor suppressor Rb. In the 1990's, it is discovered that small molecular cell growth regulator controls cell division process(i.e. growth, differentiation, cytogenesis, aging and apoptosis etc.) through its own regulatory function. These results were very useful for more precise understanding of the pathology of several diseases.

A representative example is cancer. In transformation process from normal cells to cancer cells, it was frequently observed that cell growth regulator loses its own function. That is to say, in cancer cells, the cell growth regulator shows an abnormal activity, which is deeply associated with invasion/metastasis which is crucial in the cancerpathology. Particularly, cell cycle deregulation is recognized to be a direct cause of cancer since cancer occurs in experimental animal when overexpression or knock-out of cell growth regulator is induced by using tranformed animal.

The cell growth is under positive or negative regulation in the same manner as other biological regulations. The major pathway of cell cycle regulation known up to now is based on CDK activity and, as a result of studies on many cancer cells and carcinogenesis mechanisms, it was confirmed that problems of positive or negative regulation on CDK activity result in carcinogenesis in many cases. That is, cancer may occur when positive or negative regulation and timely regulation which is important for cell growth regulation are disrupted.

The representative CDKs of mammals are CDK4(Cyclin dependent kinase 4) and CDK2 which show their activity in G1-S phase of cell cycle, CDC2(CDK1) which shows its activity in G2-M phase, and so on. It is known that CDK4 and CDK2 activities are regulated by check point of G1-S cell cycle and CDC2 activity by check point of G2-M. In many cancer cells, abnormalities appear in the regulatory mechanism of CDK4, CDK2 and CDC2(CDK1) and in fact, it was confirmed that induced abnormalities cause cancer in the transformed animal. Therefore, CDK4, CDK2 and CDC2(CDK1) among several kinds of CDKs are suitable as a target of anti-cancer agents.

The results of studies on relation between these CDKs and carcinogenesis will be explained in more detail in the following, The relation between the abnormal regulation of CDK4 activity and carcinogenesis is observed in several cancer tissues. The deletion of p16 and p15 genes generating proteins which inhibit CDK4 activity and the overexpression of cyclin D1 indispensable for CDK4 activity are observed in several kinds of cancer, which suggests that malignant phenotype may be expressed when CDK4 activity is deregulated. Furthermore, it was reported that p16 knocked-out mouse has such a high carcinogenesis rate as p53 knocked-out mouse, which suggests that malfunction of p16 on CDK4 regulation is a cause of carcinogenesis. From these experimental results, deregulation of CDK4 activity may be a cause of carcinogenesis and play a role in maintenance of phenotype of cancer cell. Therefore, CDK4 inhibitors may have anti-cancer effects.

It was reported that overexpression of cyclin E indispensible for CDK2 activity is observed in some breast cancers, deeply associated with metastasis of breast cancer, inhibits cell apoptosis under low serum condition and induces anchorage independent growth, and that hyperproliferation and neoplasia of mammary epithelial cells are observed in transformed animal with overexpressed CDK2 by MMTV promoter, which suggests that CDK2 activity is related with the progress or maintenance of cell transformation and CDK2 inhibitors may also have anti-cancer effects.

Furthermore, it is discovered that CDC2(CDK1), CDK3, CDK5, CDK6 and CDK7 play an important role in each phase of cell division. These are classified into CDKs family. In addition to cyclin D1 and E, cyclin A, B, C, D2, D3, D4, F and G are also calssified into the same family.

On the basis of the above-mentioned research, efficient inhibitors of these CDKs may be useful as anti-cancer agents. Therefore, recently, these inhibitors have been developed.

As effective CDK inhibitors developed hitherto, there exists Flavopiridol, compound of the formula (A):

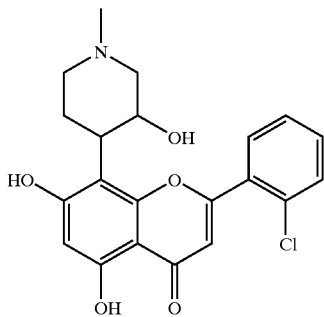

(A)

[Ref.: EP 0,241,003(1987) and 0,336,061(1990)].

In addition, a purine derivative of the formula (B):

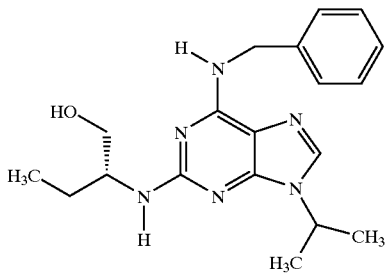

(B)

has been recently developed[Ref: WO 97/20842].

Recently, a CDKs inhibitor having aminopyridine structure of the formula (C):

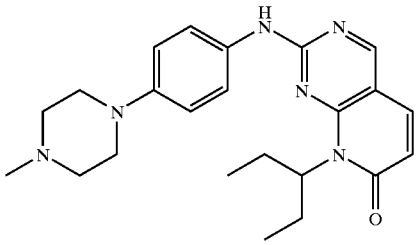

(C)

is disclosed in WO 98/33798.

However, the CDK inhibitors developed up to now could not have satisfactory effects.

So, the present inventors have made widespread and concentrative researches on CDK inhibitors, particularly indazole-based compounds, and as a result, found that a component of the formula (1) which has a quite different structure from any other known CDK inhibitors inhibits CDKs enzymes effectively and finally, completed the present invention.

DISCLOSURE OF THE INVENTION

The object of the present invention is to provide a novel indazole derivative of formula (1), a process for preparing the same, and a composition for inhibiting and treating diseases involving cell proliferation such as cancer, inflammation, restenosis and angiogenesis which comprises as an active ingredient the compound of formula (1). In this specification, CDKs include all of CDK2, CDK4, CDC2 (CDK1), CDK3, CDK5, CDK6, CDK7 etc., and cyclin includes cyclin D1, E, A, B, C, D2, D3, D4, F and G

DETAILED DESCRIPTION OF THE INVENTION

Hereinafter, the present invention is explained in detail.

The present invention relates to a novel indazole derivative represented by the following formula (1):

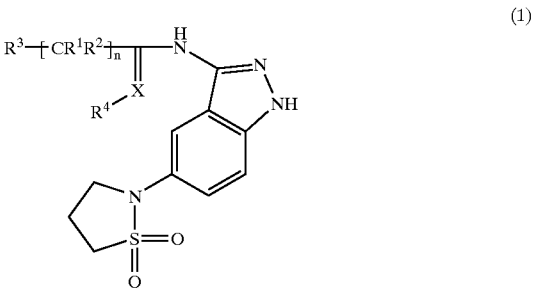

(1)

in which n represents 0, 1, 2 or 3,

X represents oxygen, sulfur or nitrogen atom, $R^1$ and $R^2$ each independently represent hydrogen, amino, hydroxy, lower alkyl or cycloalkyl, or together form cycloalkyl, $R^3$ represents hydrogen; lower alkyl; phenyl or naphthyl which may be unsubstituted or substituted with one to three substituents selected from the group consisting of hydroxy, halogen, nitro, amide, ester, carboxy, cyano, amidinyl, —O—$R^5$, —N $R^6$ $R^7$, phenyl, alkylsulfanyl, $R^8$—$SO_2$—, lower alkyl, lower alkyl substituted with $R^9$, pyridinyl, piperidinyl, morpholinyl, piperazinyl, thienyl and furyl; aromatic and bicyclic aromatic compounds bearing at least one heteroatom selected from nitrogen, oxygen or sulfur atom; $C_{3-7}$-cycloalkyl bearing at least one heteroatom selected from nitrogen, oxygen or sulfur atom; piperazinyl, imidazolyl, morpholinyl or piperadinyl which may be unsubstituted or substituted with one or two substituents selected from the group consisting of lower alkyl, phenyl, phenyl substituted with halogen, phenyl substituted with alkoxy, phenyl substituted with alkylcarbonyl, biphenyl and naphthyl; thiazole which may be unsubstituted or substituted with amino, mono- or di-lower alkylamino, alkylcarbonylamino, benzylamino, benzyloxycarbonylamino, benzyloxybenzylamino or alkoxycarbonylamino; benzodioxol; isoquinoline; indolyl; or benzimidazole wherein $R^5$ represents phenyl, benzyl, lower alkyl, alkoxyalkyl, alkoxyalkoxylalkyl, alkoxyalkoxyalkoxyalkyl, aminoalkyl or mono- or di-alkylaminoalkyl, $R^6$ and $R^7$ are identical or different from each other and represent hydrogen, lower alkyl, oxygen or benzyl, or joined to form a ring, and $R^8$ and $R^9$ represent each independently lower alkyl, amino, morpholinyl, piperazinyl, N-alkylpiperazinyl or imidazole, and $R^4$ represents nothing when X is oxygen or sulfur atom, but represents hydroxy or alkoxy when X is nitrogen atom, pharmaceutically acceptable salt, solvated product and isomer thereof which have efficacies on inhibiting and treating diseases involving cell proliferation such as cancer, inflammation, restenosis and angiogenesis through a mechanism of inhibiting CDKs activity.

Among the indazole derivatives of formula (1) according to the present invention, the preferred compounds include those wherein n represents 1 or 2, X represents oxygen, sulfur or nitrogen atom, $R^1$ and $R^2$ each independently represent hydrogen, amino, hydroxy, lower alkyl or cycloalkyl, or together form cycloalkyl, $R^3$ represents hydrogen; lower alkyl; phenyl which may be unsubstituted or substituted with one to three substituents selected from the group consisting of hydroxy, halogen, nitro, amide, cyano, amidinyl, —O—$R^5$, —N $R^6$ $R^7$, phenyl, lower alkylsulfanyl, $R^8$—$SO_2$—, lower alkyl, lower alkyl substituted with $R^9$, pyridiny, piperidinyl, morpholinyl, thienyl and furyl; naphthyl; piperazinyl or imidazolyl which may be unsubstituted or substituted with one or two substituents selected from the group consisting of lower alkyl, phenyl, phenyl substituted with halogen, phenyl substituted with lower alkoxy, phenyl substituted with acetyl, biphenyl and naphthyl; morpholinyl; piperidinyl; thiazole which may be unsubstituted or substituted with amino, mono- or di-lower alkylamino, acetylamino, benzylamino, benzyloxyamino, benzyloxybenzylamino or lower alkoxycarbonylamino; benzodioxol; 3,4-dihydroisoquinoline; or benzimidazole wherein $R^5$ represents phenyl, benzyl, lower alkyl, lower alkoxyalkyl, polyethyleneglycolyl, aminoalkyl or mono- or di-lower alkylaminoalkyl, $R^6$ and $R^7$ are identical or different from each other and represent hydrogen, lower alkyl, oxygen or benzyl, or joined to form a ring, and R8 and $R^9$ each independently represent lower alkyl, amino, morpholinyl, piperazinyl, N-alkylpiperazinyl or imidazole, and $R^4$ represents nothing when X is oxygen or sulfur atom, but represents hydroxy or alkoxy when X is nitrogen atom.

The term "lower alkyl" in the substituents of the compound of formula (1) refers to a linear or branched saturated radical of from 1 to 6 C atoms such as methyl, ethyl, isopropyl, isobutyl and t-butyl. The term "lower alkoxy" refers to a linear or branched radical of from 1 to 6 C atoms such as methoxy, ethoxy, isopropoxy, isobutoxy and t-butoxy.

Since the compounds of formula (1) according to the present invention may have asymmetric carbon centers, they can be present in the form of enantiomer or diastereomer, and mixtures thereof including racemate.

Therefore, the present invention also includes all these isomers and their mixtures.

The compound of formula (1) according to the present invention may also form a pharmaceutically acceptable salt. Such a salt includes non-toxic acid addition salt containing pharmaceutical acceptable anion, for example a salt with inorganic acids such as hydrochloric acid, sulfuric acid, nitric acid, phosphoric acid, hydrobromic acid, hydroiodic acid, etc., a salt with organic carboxylic acids such as tartaric acid, formic acid, citric acid, acetic acid, trichloroacetic acid, trifluoroacetic acid, capric acid, isobutanoic acid, oxalic acid, malonic acid, succinic acid, phthalic acid, gluconic acid, benzoic acid, lactic acid, fumaric acid, maleic acid, etc., or a salt with sulfonic acids such as methanesulfonic acid, benzenesulfonic acid, p-toluenesulfonic acid, naphthalenesulfonic acid, etc.

The representative examples of the compound of formula (1) according to the present invention are 1. N-[5-(1,1-dioxo-1$\lambda^6$-isothiazolidin-2-yl)-1H-indazol-3-yl]-2-phenylacetamide,
2. 2-(3-chlorophenyl)-N-[5-(1,1-dioxo-1$\lambda^6$-isothiazolidin-2-yl)-1H-indazol-3-yl]acetamide,
3. 2-[4-(benzyloxy)phenyl]-N-[5-(1,1-dioxo-1$\lambda^6$-isothiazolidin-2-yl)-1H-indazol-3-yl]acetamide,
4. N-[5-(1,1-dioxo-1$\lambda^6$-isothiazolidin-2-yl)-1H-indazol-3-yl]-2-(4-hydroxyphenyl)acetamide,
5. 2-[4-(dibenzylamino)phenyl]-N-[5-(1,1-dioxo-1$\lambda^6$-isothiazolidin-2-yl)-1H-indazol-3-yl]acetamide,
6. N-[5-(1,1-dioxo-1$\lambda^6$-isothiazolidin-2-yl)-1H-indazol-3-yl]-2-[4-(methylamino)phenyl]acetamide,
7. 2-(4-aminophenyl)-N-[5-(1,1-dioxo-1$\lambda^6$-isothiazolidin-2-yl)-1H-indazol-3-yl]acetamide,
8. 2-(4-chlorophenyl)-N-[5-(1,1-dioxo-1$\lambda^6$-isothiazolidin-2-yl)-1H-indazol-3-yl]acetamide,
9. N-[5-(1,1-dioxo-1$\lambda^6$-isothiazolidin-2-yl)-1H-indazol-3-yl]-2-(4-fluorophenyl)acetamide,
10. 2-[1,1'-biphenyl]-4-yl-N-[5-(1,1-dioxo-1$\lambda^6$-isothiazolidin-2-yl)-1H-indazol-3-yl]acetamide,
11. 2-(3-bromophenyl)-N-[5-(1,1-dioxo-1$\lambda^6$-isothiazolidin-2-yl)-1H-indazol-3-yl]acetamide,
12. 2-(4-bromophenyl)-N-[5-(1,1-dioxo-1$\lambda^6$-isothiazolidin-2-yl)-1H-indazol-3-yl]acetamide,
13. N-[5-(1,1-dioxo-1$\lambda^6$-isothiazolidin-2-yl)-1H-indazol-3-yl]-2-phenylethanethioamide,
14. N-[5-(1,1-dioxo-1$\lambda^6$-isothiazolidin-2-yl)-1H-indazol-3-yl]-N'-hydroxy-2-phenylethaneimidoamide,
15. 2-(1,3-benzodioxol-5-yl)-N-[5-(1,1-dioxo-1$\lambda^6$-isothiazolidin-2-yl)-1H-indazole-3-yl]acetamide,
16. N-[5-(1,1-dioxo-1$\lambda^6$-isothiazolidin-2-yl)-1H-indazol-3-yl]-2-(1-naphthyl)acetamide, 17. N-[5-(1,1-dioxo-1λ$^6$-isothiazolidin-2-yl)-1H-indazol-3-yl]-2-(2-naphthyl)acetamide,
18. N-[5-(1,1-dioxo-1λ$^6$-isothiazolidin-2-yl)-1H-indazol-3-yl]-2-(3-nitrophenyl)acetamide,
19. N-[5-(1,1-dioxo-1λ$^6$-isothiazolidin-2-yl)-1H-indazol-3-yl]acetamide,
20. N-[5-(1,1-dioxo-1λ$^6$-isothiazolidin-2-yl)-1H-indazol-3-yl]-2-[4-(methylsulfanil)phenyl]acetamide,
21. 2-(3-aminophenyl)-N-[5-(1,1-dioxo-1λ$^6$-isothiazolidin-2-yl)-1H-indazol-3-yl]acetamide,
22. N-[5-(1,1-dioxo-1λ$^6$-isothiazolidin-2-yl)-1H-indazol-3-yl]ethanethioamide,
23. N-[5-(1,1-dioxo-1λ$^6$-isothiazolidin-2-yl)-1H-indazol-3-yl]-N'-hydroxyethaneimidoamide,
24. 2-(3,4-dichlorophenyl)-N-[5-(1,1-dioxo-1λ$^6$-isothiazolidin-2-yl)-1H-indazol-3-yl]acetamide,
25. N-[5-(1,1-dioxo-1λ$^6$-isothiazolidin-2-yl)-1H-indazol-3-yl]-3-phenylpropanamide,
26. N-[5-(1,1-dioxo-1λ$^6$-isothiazolidin-2-yl)-1H-indazol-3-yl]-2-(4-isopropylphenyl)acetamide,
27. N-[5-(1,1-dioxo-1λ$^6$-isothiazolidin-2-yl)-1H-indazol-3-yl]-2-(3-methylphenyl)acetamide,
28. N-[5-(1,1-dioxo-1λ$^6$-isothiazolidin-2-yl)-1H-indazol-3-yl]-2-(4-methylphenyl)acetamide,
29. N-[5-(1,1-dioxo-1λ$^6$-isothiazolidin-2-yl)-1H-indazol-3-yl]-2-[4-(methylsulfonyl)phenyl]acetamide,
30. N-[5-(1,1-dioxo-1λ$^6$-isothiazolidin-2-yl)-1H-indazol-3-yl]-2-(4-methyl-1-piperazinyl)acetamide,
31. N-[5-(1,1-dioxo-1λ$^6$-isothiazolidin-2-yl)-1H-indazol-3-yl]-2-(4-morpholinyl)acetamide,
32. N-[5-(1,1-dioxo-1λ$^6$-isothiazolidin-2-yl)-1H-indazol-3-yl]-2-(1-piperidinyl)acetamide,
33. N-[5-(1,1-dioxo-1λ$^6$-isothiazolidin-2-yl)-1H-indazol-3-yl]-2-[4-(4-pyridinyl)phenyl]acetamide,
34. N-[5-(1,1-dioxo-1λ$^6$-isothiazolidin-2-yl)-1H-indazol-3-yl]-2-[4-(1-piperidinyl)phenyl]acetamide,
35. N-[5-(1,1-dioxo-1λ$^6$-isothiazolidin-2-yl)-1H-indazol-3-yl]-2-[4-(1-morpholinyl)phenyl]acetamide,
36. N-[5-(1,1-dioxo-1λ$^6$-isothiazolidin-2-yl)-1H-indazol-3-yl]-2-[4-(3-thienyl)phenyl]acetamide,
37. N-[5-(1,1-dioxo-1λ$^6$-isothiazolidin-2-yl)-1H-indazol-3-yl]-2-[4-(4-morpholinylsulfonyl)phenyl]acetamide,
38. N-[5-(1,1-dioxo-1λ$^6$-isothiazolidin-2-yl)-1H-indazol-3-yl]-2-(4-methoxyphenyl)acetamide,
39. N-[5-(1,1-dioxo-1λ$^6$-isothiazolidin-2-yl)-1H-indazol-3-yl]-2-[4-(2-furyl)phenyl]acetamide,
40. N-[5-(1,1-dioxo-1λ$^6$-isothiazolidin-2-yl)-1H-indazol-3-yl]-2-4-[(4-methyl-1-piperazinyl)sulfonyl]phenylacetamide,
41. 2-(1H-benzimidazol-1-yl)-N-[5-(1,1-dioxo-1λ$^6$-isothiazolidin-2-yl)-1H-indazol-3-yl]acetamide,
42. N-[5-(1,1-dioxo-1λ$^6$-isothiazolidin-2-yl)-1H-indazol-3-yl]-2-(4-ethoxyphenyl)acetamide,
43. N-[5-(1,1-dioxo-1λ$^6$-isothiazolidin-2-yl)-1H-indazol-3-yl]-2-[4-(4-morpholinylmethyl)phenyl]acetamide,
44. N-[5-(1,1-dioxo-1λ$^6$-isothiazolidin-2-yl)-1H-indazol-3-yl]-2-4-[(4-methyl-1-piperazinyl)methyl]phenylacetamide,
45. N-[5-(1,1-dioxo-1λ$^6$-isothiazolidin-2-yl)-1H-indazol-3-yl]-2-(4-nitrophenyl)acetamide,
46. N-[5-(1,1-dioxo-1λ$^6$-isothiazolidin-2-yl)-1H-indazol-3-yl]-2-[4-(1H-imidazole-1-ylmethyl)phenyl]acetamide,
47. N-[5-(1,1-dioxo-1λ$^6$-isothiazolidin-2-yl)-1H-indazol-3-yl]-2-(4-phenyl-1H-imidazol-1-yl)acetamide,
48. N-[5-(1,1-dioxo-1λ$^6$-isothiazolidin-2-yl)-1H-indazol-3-yl]-2-(4-phenyl-1-piperazinyl) acetamide,
49. 2-[3,4-dihydro-2(1H)-isoquinolinyl]-N-[5-(1,1-dioxo-1λ$^6$-isothiazolidin-2-yl)-1H-indazol-3-yl]acetamide,
50. N-[5-(1,1-dioxo-1λ$^6$-isothiazolidin-2-yl)-1H-indazol-3-yl]-2-[4-(4-chlorophenyl)-1-piperazinyl]acetamide,
51. N-[5-(1,1-dioxo-1λ$^6$-isothiazolidin-2-yl)-1H-indazol-3-yl]-2-[4-(4-methoxyphenyl)-1-piperazinyl]acetamide,
52. N-[5-(1,1-dioxo-1λ$^6$-isothiazolidin-2-yl)-1H-indazol-3-yl]-2-[4-(2-ethoxyphenyl)-1-piperazinyl]acetamide,
53. 2-[4-(4-acetylphenyl)-1-piperazinyl]-N-[5-(1,1-dioxo-1λ$^6$-isothiazolidin-2-yl)-1H-indazol-3-yl]acetamide,
54. N-[5-(1,1-dioxo-1λ$^6$-isothiazolidin-2-yl)-1H-indazol-3-yl]-2-(4-phenoxyphenyl)acetamide,
55. N-[5-(1,1-dioxo-1λ$^6$-isothiazolidin-2-yl)-1H-indazol-3-yl]-1-phenylcyclopentanecarboxamide,
56. 2-cyclopentyl-N-[5-(1,1-dioxo-1λ$^6$-isothiazolidin-2-yl)-1H-indazol-3-yl]-2-phenylacetamide,
57. N-[5-(1,1-dioxo-1λ$^6$-isothiazolidin-2-yl)-1H-indazol-3-yl]-2-phenylbutanamide,
58. t-butyl 4-(2-[5-(1,1-dioxo-1λ$^6$-isothiazolidin-2-yl)-1H-indazol-3-yl]amino-2-oxoethyl)-1,3-thiazol-2-ylcarbamate,
59. N-[5-(1,1-dioxo-1λ$^6$-isothiazolidin-2-yl)-1H-indazol-3-yl]-2-4-[2-(2-ethoxyethoxy)ethoxy]phenylacetamide,
60. 2-(2-amino-1,3-thiazol-4-yl)-N-[5-(1,1-dioxo-1λ$^6$-isothiazolidin-2-yl)-1H-indazol-3-yl]acetamide,
61. 2-[4-(4-bromophenyl)-1H-imidazol-1-yl]-N-[5-(1,1-dioxo-1λ$^6$-isothiazolidin-2-yl)-1H-indazol-3-yl]acetamide,
62. N-[5-(1,1-dioxo-1λ$^6$-isothiazolidin-2-yl)-1H-indazol-3-yl]-2-[4-(2-naphthyl)-1H-imidazol-1-yl]acetamide,
63. 2-(4-[1,1'-biphenyl]-4-yl-1H-imidazol-1-yl)-N-[5-(1,1-dioxo-1λ$^6$-isothiazolidin-2-yl)-1H-indazol-3-yl]acetamide,
64. N-[5-(1,1-dioxo-1λ$^6$-isothiazolidin-2-yl)-1H-indazol-3-yl]-2-[2-(ethylamino)-1,3-thiazol-4-yl]acetamide,
65. 2-[2-(diethylamino)-1,3-thiazol-4-yl]-N-[5-(1,1-dioxo-1λ$^6$-isothiazolidin-2-yl)-1H-indazol-3-yl]acetamide,
66. N-[5-(1,1-dioxo-1λ$^6$-isothiazolidin-2-yl)-1H-indazol-3-yl]-2-(4-2-[2-(2-methoxyethoxy)ethoxy]ethoxyphenyl)acetamide,
67. N-[5-(1,1-dioxo-1λ$^6$-isothiazolidin-2-yl)-1H-indazol-3-yl]-2-(4-ethoxy-3-nitrophenyl)acetamide,
68. N-[5-(1,1-dioxo-1λ$^6$-isothiazolidin-2-yl)-1H-indazol-3-yl]-2-(2-methylphenyl)acetamide,
69. N-[5-(1,1-dioxo-1λ$^6$-isothiazolidin-2-yl)-1H-indazol-3-yl]-2-[3-(ethylamino)phenyl]acetamide,
70. 2-[3-(diethylamino)phenyl]-N-[5-(1,1-dioxo-1λ$^6$-isothiazolidin-2-yl)-1H-indazol-3-yl]acetamide,
71. 2-(3,5-dimethoxyphenyl)-N-[5-(1,1-dioxo-1λ$^6$-isothiazolidin-2-yl)-1H-indazol-3-yl]acetamide,
72. N-[5-(1,1-dioxo-1λ$^6$-isothiazolidin-2-yl)-1H-indazol-3-yl]-2-[4-(ethylamino)phenyl]acetamide,
73. 2-[4-(diethylamino)phenyl]-N-[5-(1,1-dioxo-1λ$^6$-isothiazolidin-2-yl)-1H-indazol-3-yl]acetamide, 74. 2-(3-chloro-4-ethoxyphenyl)-N-[5-(1,1-dioxo-1$\lambda^6$-isothiazolidin-2-yl)-1H-indazol-3-yl]acetamide, 75. 2-[4-(2-aminoethoxy)phenyl]-N-[5-(1,1-dioxo-1$\lambda^6$-isothiazolidin-2-yl)-1H-indazol-3-yl]acetamide, 76. 2-[2-(acetylamino)-1,3-thiazol-4-yl]-N-[5-(1,1-dioxo-1$\lambda^6$-isothiazolidin-2-yl-1H-indazol-3-yl]acetamide, 77. 2-(2-[4-(benzyloxy)benzyl]amino-1,3-thiazol-4-yl)-N-[5-(1,1-dioxo-1$\lambda^6$-isothiazolidin-2-yl)-1H-indazol-3-yl]acetamide, 78. N-[5-(1,1-dioxo-1$\lambda^6$-isothiazolidin-2-yl)-1H-indazol-3-yl]-2-(3-ethoxyphenyl)acetamide, 79. N-[5-(1,1-dioxo-1$\lambda^6$-isothiazolidin-2-yl)-1H-indazol-3-yl]-2-[4-ethoxy-3-(4-morpholinylsulfonyl)phenyl]acetamide, 80. 2-[3-(aminosulfonyl)-4-ethoxyphenyl]-N-[5-(1,1-dioxo-1$\lambda^6$-isothiazolidin-2-yl)-1H-indazol-3-yl]acetamide, 81. N-[5-(1,1-dioxo-1$\lambda^6$-isothiazolidin-2-yl)-1H-indazol-3-yl]-2-4-ethoxy-3-[(4-methyl-1-piperazinyl)sulfonyl]phenylacetamide, and 82. 2-[4-(2-aminoethoxy)phenyl]-N-[5-(1,1-dioxo-1$\lambda^6$-isothiazolidin-2-yl)-1H-indazol-3-yl]acetamide.

The processes for preparing the compound of formula (1) as defined above are depicted in the following Scheme (1):

[Scheme 1]

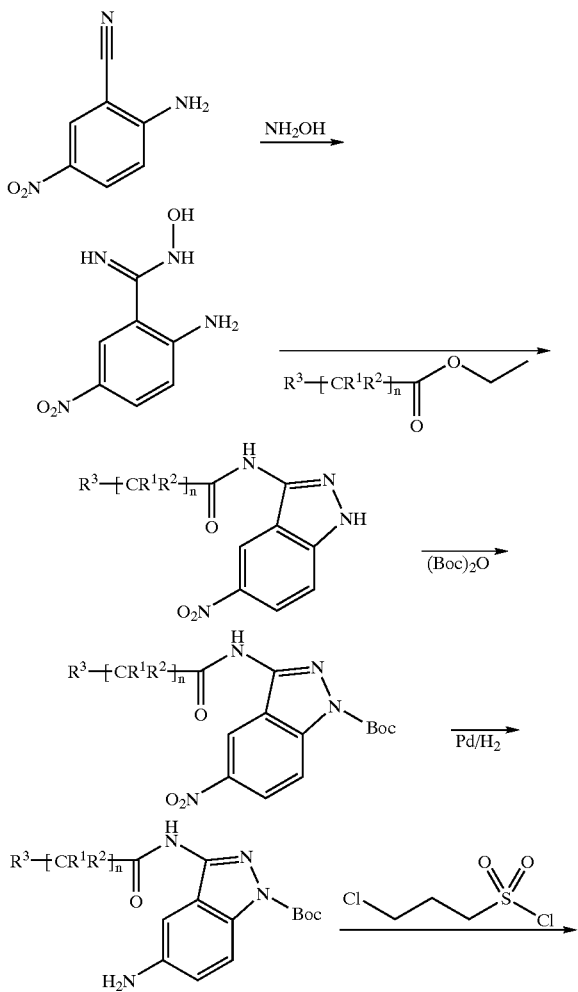

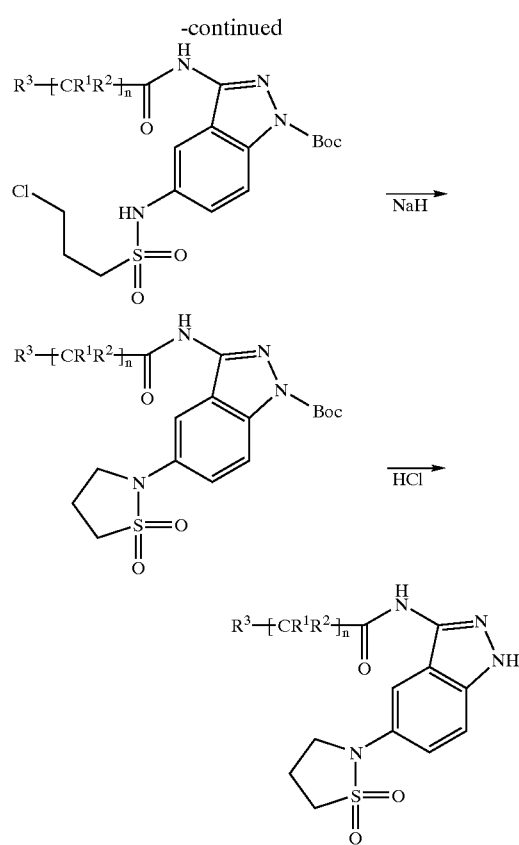

wherein $R^1$, $R^2$, $R^3$ and n are as previously described, and Boc represents t-butoxycarbonyl.

That is, as depicted in the above Scheme (1), an amidoxime of the following formula (2):

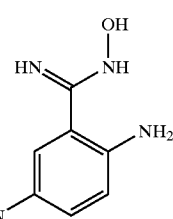

(2)

is prepared by reacting anthranilonitrile with hydroxylamine, and the amidoxime thus prepared is then reacted with ester to produce a 3-aminoindazole of the following formula (3):

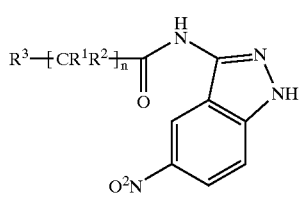

(3)

wherein $R^1$, $R^2$ and $R^3$ are as previously described.

A 1-position of 3-aminoindazole is protected by t-butylcarbamate to produce a compound of the following formula (4):

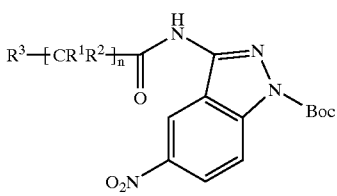

(4)

wherein $R^1$, $R^2$, $R^3$ and n are as previously described, and Boc represents t-butoxycarbonyl, and then nitro group at 5-C is reduced to produce an amine of the following formula (5):

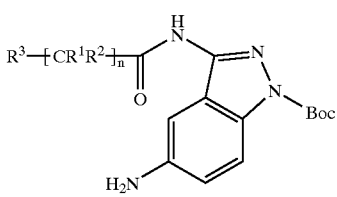

(5)

wherein $R^1$, $R^2$, $R^3$ and n are as previously described, and Boc represents t-butoxycarbonyl.

A sulfonamide of the following formula (6):

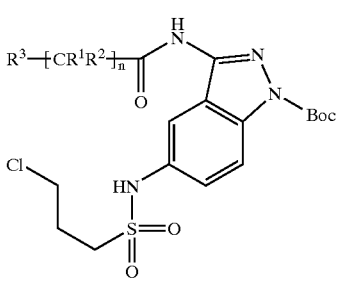

(6)

wherein $R^1$, $R^2$, $R^3$ and n are as previously described, and Boc represents t-butoxycarbonyl, which is obtained by reacting the compound of formula (5) with sulfonyl chloride is cyclized through intramolecular ring-closure to synthesize a dioxoisothiazolidine of the following formula (7):

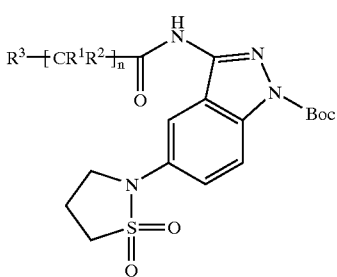

(7)

wherein $R^1$, $R^2$, $R^3$ and n are as previously described, and Boc represents t-butoxycarbonyl.

Finally, the compound of formula (7) is deprotected to give the compound of formula (1). A compound of formula (1) wherein X is oxygen atom is reacted with Lawesson's reagent (2,4-bis-(4-methoxyphenyl-1,3-dithia-2,4-diphosphethane-2,4-disulfide) to produce a compound of formula (1) wherein X is sulfur atom, or the compound of formula (1) wherein X is sulfur atom is reacted with a compound of the following formula (8):

(8)

wherein $R^4$ is as previously described, to produce a compound of formula (1) wherein X is nitrogen atom:

The indazole derivative of formula (1) according to the present invention may also be synthesized through amidization followed by deprotection of an indazole intermediate of the following formula (9):

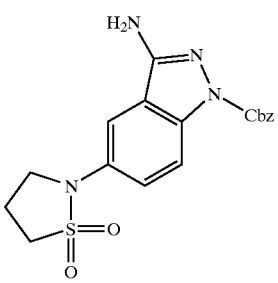

(9)

wherein Cbz represents benzyloxycarbonyl.

Specifically, the indazole intermediate of formula (9) is reacted with an acyl halide of the following formula (10):

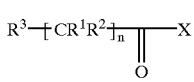

(10)

wherein $R^1$, $R^2$, $R^3$ and n are as previously described in the formula (1), and X' represents halogen, for example, Cl, or Br., and then subjected to deprotection to give the compound of formula (1), which will be described in the following Example 2.

Meanwhile, the indazole derivative of formula (9) is prepared by using anthranilonitrile as a starting material, as depicted in the following Scheme (2):

[Scheme 2]

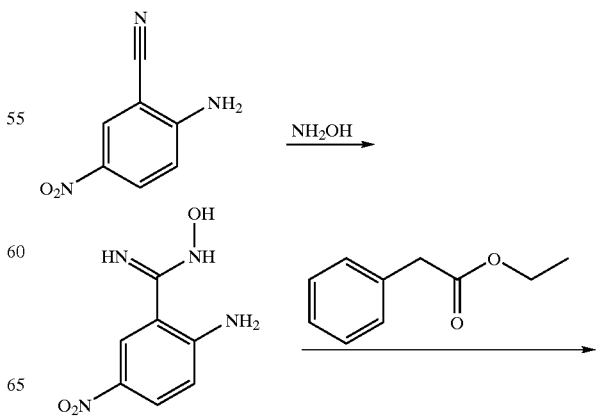

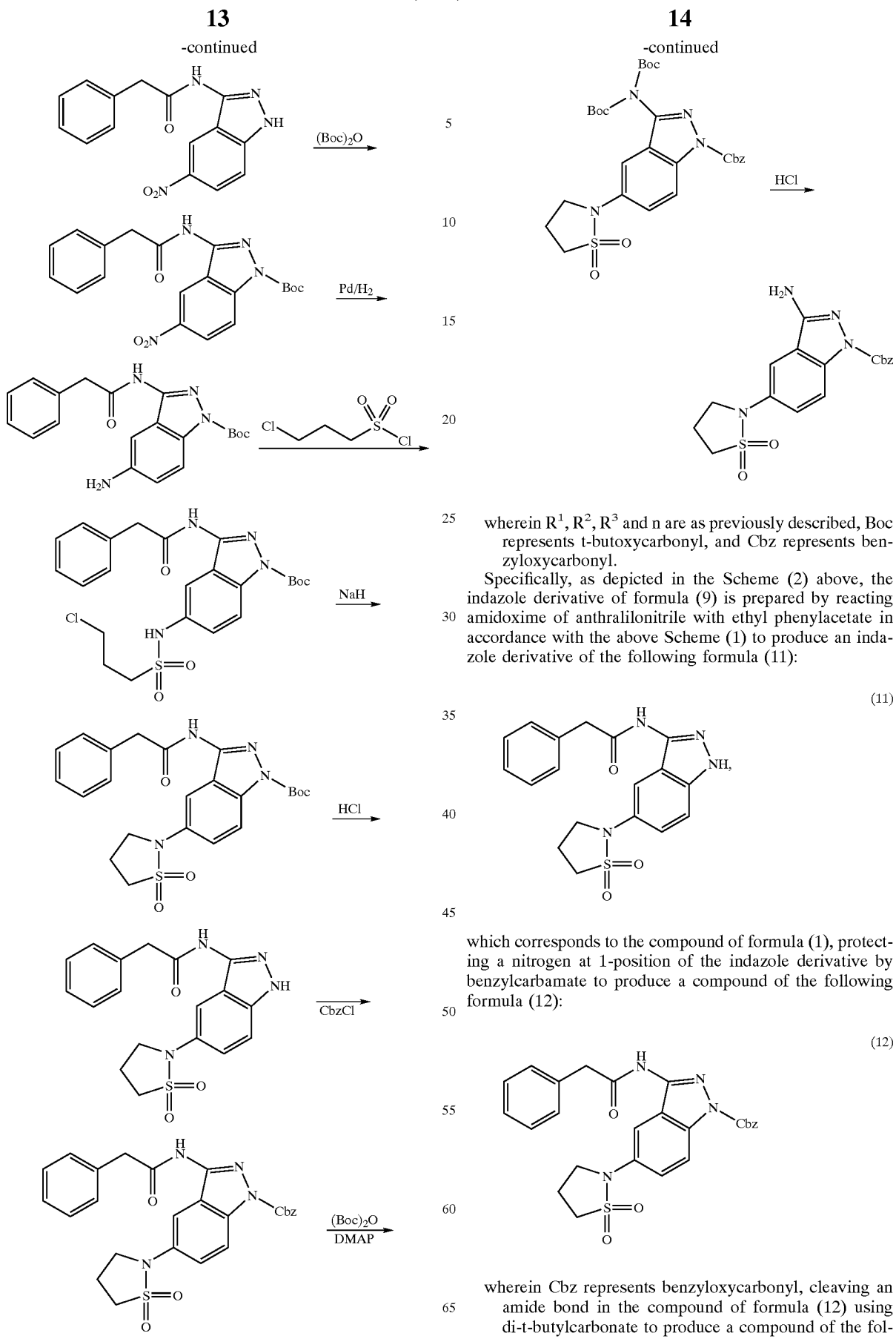

wherein $R^1$, $R^2$, $R^3$ and n are as previously described, Boc represents t-butoxycarbonyl, and Cbz represents benzyloxycarbonyl.

Specifically, as depicted in the Scheme (2) above, the indazole derivative of formula (9) is prepared by reacting amidoxime of anthralilonitrile with ethyl phenylacetate in accordance with the above Scheme (1) to produce an indazole derivative of the following formula (11):

which corresponds to the compound of formula (1), protecting a nitrogen at 1-position of the indazole derivative by benzylcarbamate to produce a compound of the following formula (12):

wherein Cbz represents benzyloxycarbonyl, cleaving an amide bond in the compound of formula (12) using di-t-butylcarbonate to produce a compound of the following formula (13):

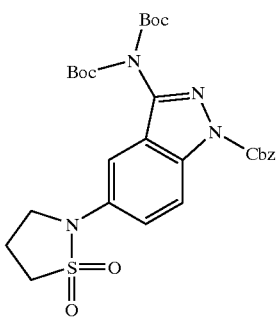

(13)

wherein Boc represents t-butoxycarbonyl, and Cbz represents benzyloxycarbonyl, and removing t-butoxycarbonyl groups.

However, the process for preparing the compounds according to the present invention has been described in detail for the purpose of illustration, but should not be interpreted to limit the invention. The compounds of the present invention can easily be prepared by conventional methods of organic synthesis described in the prior art or combinations thereof, and such combinations are well known to those skilled in the art.

The compound of the formula (1) according to the present invention has an inhibitory activity against CDK, and thus may be put to a good use as an agent for inhibiting and treating diseases involving cell proliferation such as cancer, inflammation, restenosis and angiogenesis. Accordingly, another object of the present invention is to provide a composition for inhibiting and treating diseases involving cell proliferation such as cancer, inflammation, restenosis and angiogenesis which comprises the compound of formula (1), pharmaceutically acceptable salt, solvated product or isomer thereof as an active ingredient together with a pharmaceutically acceptable carrier.

When the compound of the present invention is administered for clinical purpose, it is preferably administered in an amount ranging from 1.0 to 50 mg/kg of body weight a day. The total daily dosage may be administered in one time or over several times. However, the specific dosage for a specific patient can be varied according to the specific compound used, body weight of the subject patient, sex, hygienic condition, diet, time or method of administration, excretion rate, mixing ratio of the medicine, severity of the disease to be treated, etc.

The compound of the present invention may be administered in the form of injections or oral preparations.

Injections such as sterilized aqueous or oily suspension for injection may be prepared by using suitable dispersing agent, sufactant or suspension agent according to the known method. As solvents to be used for preparing injections, water, Ringer's fluid and isotonic NaCl solution can be mentioned, and sterilized fixing oil is also used as the solvent or suspension medium. Any non-stimulative fixing oil including mono- or di-glyceride can be used for this purpose, and also fatty acid such as oleic acid can be used for injection formulation.

As the solid preparation for oral administration, capsules, tablets, pills, powders and granules, preferably capsules and tablets can be mentioned. It is desirable for tablets and pills to be formulated into enteric-coated preparation. Solid preparations may be prepared by mixing the active compound of formula (1) according to the present invention with at least one carrier selected from the group consisting of inert diluents(e.g. sucrose, lactose, starch, etc.), lubricants (e.g. magnesium stearate), disintegrants, and binders.

When it is intended to produce the desired anti-cancer effects by administering clinically the compound of the invention, the active compound of the formula (1) can be administered together with at least one agent selected from the known anti-cancer agents. In this manner, as anti-cancer agents to be administered with the compound of the invention, 5-fluorouracil, cisplatin, doxorubicin, taxol, gemcitabine, etc. can be mentioned.

However, the preparations containing the compound according to the invention intended for anti-cancer effect are not limited to those described above, and any preparations useful for treating and inhibiting cancers can be included.

The present invention is more specifically explained by way of the following prepartions and examples. However, it should be understood that the present invention is not limited to these examples in any manner.

Preparation 1

Synthesis of t-Butyl 5-(1,1-Dioxo-1$\lambda^6$-isothiazolidin-2-yl)-3-[(2-phenylacetyl)amino]-1H-indazol-1-carboxylate 1-1) Synthesis of 2-Amino-N-hydroxy-5-nitrobenzenecarboxyimidoamide 27.8 g (400 mmol) of hydroxylamine hydrochloride and 33.6 g (400 mmol) of sodium bicarbonate were dissolved in 140 ml of water, and then a solution of 33.6 g (200 mmol) of anthranilonitrile in 520 ml of ethanol was added thereto. The mixture was heated under reflux for 12 hours, and then cooled to room temperature. The resulting precipitate was filtered and washed with water and diethyl ether to give 37.2 g of the title compound in a yield of 95%.

$^1$H NMR (DMSO-$d_6$, ppm): δ 6.02 (2H, s), 7.78 (1H, d), 7.80 (2H, s), 7.92 (1H, dd), 8.35 (1H, d), 9.98 (1H, s); FAB MS(m/e)=197[M+1].

1-2) Synthesis of N-(5-Nitro-1H-indazol-3-yl)-2-phenylacetamide 29.4 g (150 mmol) of the compound obtained in Preparation 1-1) was dissolved in 500 ml of tetrahydrofuran, and 9.0 g (60%, 225 mmol) of sodium hydride was added thereto. The mixture was stirred at room temperature for 30 minutes. 36.9 g (225 mmol) of ethyl phenylacetate was added thereto, the mixture was stirred for one hour, and then 200 ml of N,N-dimethylformamide was added thereto. The mixture was further stirred under slight heating for 4 hours. The solvent was removed under reduced pressure, and the residue was then treated with ethyl acetate and water. The resulting precipitate was filtered and washed with water and diethyl lether to give 20.3 g of the title compound in a yield of 48%.

$^1$H NMR (DMSO-$d_6$, ppm): δ 3.79 (2H, s), 7.28 (1H, t), 7.30–7.43 (4H, m), 7.60 (1H, d), 8.12 (1H, dd), 9.00 (1H, s); FAB MS(m/e)=283 [M+1].

1-3) Synthesis of t-Butyl 5-Nitro-3-[(2-phenylacetyl)amino]-1H-indazol-1-carboxylate 8.0 g (28 mmol) of the compound obtained in Preparation 1-2) was dissolved in 130 Ml of tetrahydrofuran, and 3.2 g (80 mmol) of sodium hydroxide in 20 ml of water and 7.1 g (33 mmol) of di-t-butylcarbonate were added thereto. The mixture was stirred for one hour. After removal of solvents under reduced pressure, the residue was subjected to recrystalization using ethyl acetate and hexane to give the title compound quantatively.

$^1$H NMR(CDCl$_3$, ppm): δ 1.69 (9H, s), 3.65 (2H, s), 7.24–7.30 (5H, m), 7.68 (1H, dd), 7.91 (1H, s), 8.00 (1H, d), 8.73 (1H, s).

1-4) Synthesis of t-Butyl 5-Amino-3-[(2-phenylacetyl) amino]-1H-indazol-1-carboxylate 11 g (28 mmol) of the compound obtained in Preparation 1-3) was dissolved in methanol, and palladium-adsorbed activated carbon (10%) was added thereto. The mixture was stirred under hydrogen atmosphere for 2 hours. The resulting suspension was filtered through celite, and then the filtrate was concentrated to give the title compound quantatively.

$^1$H NMR (CDCl$_3$, ppm): δ 1.68 (9H, s), 3.68 (2H, s), 7.25–7.31 (5H, m), 7.45 (1H, dd), 7.71 (1H, s), 7.94 (1H, d), 8.64 (1H, s).

1-5) Synthesis of t-Butyl 5-[[(3-Chloropropyl)sulfonyl] amino]-3-[(2-phenylacetyl)amino]-1H-indazol-1-carboxylate 6.3 g (17 mmol) of the compound obtained in Preparation 1-4) was dissolved in 120 Ml of dichloromethane, and 13 ml(170 mmol) of pyridine and 27 ml (22 mmol) of 3-chloropropanesulfonyl chloride were added thereto. The mixture was stirred at room temperature for 2 hours. The solvent was removed under reduced pressure, and then the residue was purified by silica gel column chromatography (eluent:n-hexane/ethylacetate=1/1 (v/v)) to give the title compound quantatively.

$^1$H NMR (CD$_3$OD, ppm): δ 1.69 (9H, s), 2.20 (2H, m), 3.17 (2H, t), 3.65 (4H, m), 7.29 (5H, m), 7.30 (1H, m), 7.40 (1H, d), 7.60 (1H, s); ESI MS(m/e)=507 [M+1].

1-6) Synthesis of t-Butyl 5-(1,1-Dioxo-1λ$^6$-isothiazolidin-2-yl)-3-[(2-phenylacetyl)amino]-1H-indazol-1-carboxylate 8.6 g (17 mmol) of the compound obtained in Preparation 1-5) was dissolved in 150 Ml of N,N-dimethylformamide, and 1.43 g(34 mmol) of sodium hydride was added thereto. The mixture was stirred for 30 minutes. The solvent was removed under reduced pressure. The residue was extracted with ethyl acetate, and then the extracted ethyl acetate solution was washed with water three times. The solvent was under reduced pressure, and then the residue was purified by silica gel column chromatography(eluent:n-hexane/ ethylacetate=1/2(v/v)) to give 8.0 g of the title compound quantatively.

$^1$H NMR (CDCl$_3$, ppm): δ 1.70 (9H, s), 2.50 (2H, m), 3.28 (2H, t), 3.80 (4H, m), 7.30 (5H, m), 7.68 (1H, m), 7.91 (1H, s), 8.00 (1H, d), 8.73 (1H, s); ESI MS(m/e)=471 [M+1].

Example 1

Synthesis of N-[5-(1,1-Dioxo-1λ$^6$-isothiazolidin-2-yl)-1H-indazol-3-yl]-2-phenylacetamide(1)

5.2 g (11 mmol) of the compound obtained in Preparation 1-6) was added to ethyl acetate which was saturated with hydrogen chloride, and the mixture was stirred for 6 hours. The solvent was removed under reduced pressure to give the title compound quantatively.

$^1$H NMR (DMSO-d$_6$, ppm): δ 2.39 (2H, m), 3.46 (2H, t), 3.69 (2H, t), 3.74 (2H, s), 7.26 (1H, t), 7.34 (3H, t), 7.39 (2H, d), 7.46 (1H, d), 7.58 (1H, s), 10.69 (1H, s); ESI MS(m/e)= 371 [M+1].

Preparation 2

Synthesis of Benzyl 3-Amino-5-(1,1-dioxo-1λ$^6$-isothiazolidin-2-yl)-1H-indazol-1-carboxylate (indazole Intermediate of Formula (9))

2-1) Synthesis of Benzyl 5-(1,1-Dioxo-1λ$^6$-isothiazolidin-2-yl)-3-[(2-phenylacetyl)amino]-1H-indazol-1-carboxylate After 4.1 g(11 mmol) of the compound obtained in Example 1 was dissolved in 150 Ml of dichloromethane, 10 ml(7.9 mmol) of triethylamine and 2.25 ml (17 mmol) of benzyl chloroformate were added. The mixture was stirred for 2 hours. After removal of solvent under reduced pressure, the residue was purified by silica gel column chromatography(eluent:n-hexane/ethylacetate=2/1(v/v)) to give 5.2 g of the title compound in a yield of 94%.

$^1$H NMR (DMSO-d$_6$, ppm): δ 2.34 (2H, m), 3.52 (2H, t), 3.74 (2H, t), 3.78 (2H, s), 5.48 (2H, s), 7.25 (1H, m), 7.36 (4H, m), 7.44 (3H, m), 7.53 (2H, d), 7.58 (1H, dd), 7.82 (1H, s), 8.12 (1H, d); ESI MS(m/e)=505 [M+1].

2-2) Synthesis of Benzyl 3-[bis(t-Butoxycarbonyl)amino]-5-(1,1-dioxo-1λ$^6$-isothiazolidin-2-yl)-1H-indazol-1-carboxylate After 5.2 g (11 mmol) of the compound obtained in Preparation 2-1) was dissolved in 100 Ml of dichloromethane, 1.36 g (11 mmol) of N,N-dimethylaminopyridine, 1.55 ml (11 mmol) of triethylamine and 4.85 g(22 mmol) of di-t-butylcarbonate were added. The mixture was stirred for 30 minutes. After removal of solvent under reduced pressure, the residue was purified by silica gel column chromatography(eluent:n-hexane/ethylacetate=1/2 (v/v)) to give 6.4 g of the title compound quantatively.

$^1$H NMR (CD$_3$OD, ppm): δ 1.36 (9H, s), 1.44 (9H, s), 2.51 (2H, m), 3.45 (2H, t), 3.83 (2H, t), 5.53 (2H, s), 7.34 (3H, m), 7.48 (1H, d), 7.54 (2H, d), 7.56 (1H, dd); 8.15 (1H, dd), ESI MS(m/e)=587 [M+1].

2-3) Synthesis of Benzyl 3-Amino-5-(1,1-dioxo-1λ$^6$-isothiazolidin-2-yl)-1H-indazol-1-carboxylate 6.4 g (11 mmol) of the compound obtained in Preparation 2-2) was added to ethyl acetate which was saturated with hydrogen chloride, and the mixture was stirred for 3 hours. The mixture was neutralized with aqueous 1N sodium hydroxide solution, and the precipitate thus obtained was filtered under reduced pressure to give 2 g of the title compound in a yield of 47%.

$^1$H NMR (DMSO-d$_6$, ppm): δ 2.45 (2H, m), 3.53 (2H, t), 3.77 (2H, t), 5.38 (2H, s), 6.42 (2H, s), 7.37 (1H, m), 7.42 (2H, m), 7.49 (3H, m), 7.71 (1H, d), 7.98 (1H, d); ESI MS(m/e)=505 [M+1].

Example 2

Synthesis of 2-(3-Chlorophenyl)-N-[5-(1,1-dioxo-1λ$^6$-isothiazolidin-2-yl)-1H-indazol-3-yl]acetamide (2)

50 mg (0.13 mmol) of the compound obtained in Preparation 2 was added to 10 ml of tetrahydrofuran, and 3.7 mg (0.2 mmol) of 3-chlorophenylacetyl chloride was added. The mixture was heated under reflux for 2 hours. After the mixture was cooled to room temperature, 2 ml of aqueous 2N sodium hydroxide solution was added. The mixture was stirred for 2 hours. The resultant was extracted with ethyl acetate, and then the extracted ethyl acetate solution was washed with water three times. After removal of solvent under reduced pressure, the residue was purified by silica gel column chromatography(eluent:n-hexane/ethylacetate=1/4 (v/v)) to give 21 mg of the title compound in a yield of 40%.

$^1$H NMR (CD$_3$OD, ppm): δ 2.49 (2H, m), 3.41 (2H, t), 3.77 (2H, t), 3.79 (2H, s), 7.28 (1H, m), 7.34 (2H, m), 7.45 (3H, m), 7.60 (1H, s); ESI MS(m/e)=405 [M+1].

Example 3

Synthesis of 2-[4-(Benzyloxy)phenyl]-N-[5-(1,1-dioxo-1λ$^6$-isothiazolidin-2-yl)-1H-indazol-3-yl] acetamide(3)

The title compound was obtained in a yield of 42% according to the same procedure as Example 2, except that 4-benzyloxyphenylacetyl chloride was used instead of 3-chlorophenylacetyl chloride.

$^1$H NMR (CD$_3$OD, ppm): δ 2.48 (2H, m), 3.87 (2H, t), 3.71 (2H, s), 3.75 (2H, t), 5.05 (2H, s), 6.95 (2H, d), 7.32 (5H, m), 7.42 (4H, m), 7.59 (1H, s); API MS(m/e)=477 [M+1].

Example 4

Synthesis of N-[5-(1,1-Dioxo-1λ$^6$-isothiazolidin-2-yl)-1H-indazol-3-yl]-2-(4-hydroxyphenyl)acetamide (4)

The title compound was obtained in a yield of 35% according to the same procedure as Preparation 1-4), except that the compound obtained in Example 3 was used instead of the compound obtained in Preparation 1-3).

$^1$H NMR (CD$_3$OD, ppm): δ 2.49 (2H, m), 3.41 (2H, t), 3.68 (2H, s), 3.75 (2H, t), 6.77 (2H, d), 7.24 (2H, d), 7.44 (2H, m), 7.53 (1H, s); ESI MS(m/e)=387 [M+1].

Example 5

Synthesis of 2-[4-(Dibenzylamino)phenyl]-N-[5-(1,1-dioxo-1λ$^6$-isothiazolidin-2-yl)-1H-indazol-3-yl]acetamide(5)

The title compound was obtained in a yield of 55% according to the same procedure as Example 2, except that 4-(N,N-dibenzylamino)phenylacetyl chloride was used instead of 3-chlorophenylacetyl chloride.

$^1$H NMR (CD$_3$OD, ppm): δ 2.45 (2H, m), 3.37 (2H, t), 3.62 (2H, s), 3.72 (2H, t), 4.62 (4H, s), 7.18 (4H, m), 7.23 (4H, m), 7.27 (4H, m), 7.43 (2H, m), 7.56 (1H, s); ESI MS(m/e)=566 [M+1].

Example 6

Synthesis of N-[5-(1,1-Dioxo-1λ$^6$-isothiazolidin-2-yl)-1H-indazol-3-yl]-2-[4-(methylamino)phenyl]acetamide(6)

The procedure was carried out according to the same procedure as Preparation 1-4), except that the compound obtained in Example 5 was used instead of the compound obtained in Preparation 1-3). Then, the residue was purified by silica gel column chromatography(eluent:n-hexane/ethylacetate=1/3(v/v)) to give the title compound in a yield of 10%.

$^1$H NMR (CD$_3$OD, ppm): δ 2.51 (2H, m), 2.76 (3H, s), 3.41 (2H, t), 3.64 (2H, s), 3.76 (2H, t), 6.63 (2H, d), 7.19 (2H, d), 7.43 (2H, m), 7.55 (1H, s); ESI MS(m/e)=400 [M+1].

Example 7

Synthesis of 2-(4-Aminophenyl)-N-[5-(1,1-dioxo-1λ$^6$-isothiazolidin-2-yl)-1H-indazol-3-yl]acetamide (7)

The title compound was obtained in a yield of 20% according to the same procedure as Example 6.

$^1$H NMR (CD$_3$OD, ppm): δ 2.51 (2H, m), 3.43 (2H, t), 3.65 (2H, s), 3.76 (2H, t), 6.72 (2H, d), 7.17 (2H, d), 7.46 (2H, br s), 7.52 (1 H, br s); ESI MS(m/e)=386 [M+1].

Example 8

Synthesis of 2-(4-Chlorophenyl)-N-[5-(1,1-dioxo-1λ$^6$-isothiazolidin-2-yl)-1H-indazol-3-yl]acetamide (8)

The title compound was obtained in a yield of 60% according to the same procedure as Example 2, except that 4-chlorophenylacetyl chloride was used instead of 3-chlorophenylacetyl chloride.

$^1$H NMR (CD$_3$OD, ppm): δ 2.47(2H, m), 3.40 (2H, t), 3.73 (2H, t), 3.77 (2H, s), 7.33 (2H, d), 7.38 (2H, d), 7.43 (2H, s), 7.56 (1H, s); ESI MS(m/e)=405 [M+1].

Example 9

Synthesis of N-[5-(1,1-Dioxo-1λ$^6$-isothiazolidin-2-yl)-1H-indazol-3-yl]-2-(4-fluorophenyl)acetamide(9)

The title compound was obtained in a yield of 60% according to the same procedure as Example 2, except that 4-fluorophenylacetyl chloride was used instead of 3-chlorophenylacetyl chloride.

$^1$H NMR (CD$_3$OD+CDCl$_3$, ppm): δ 2.18 (2H, m), 3.07 (2H, t), 3.45 (4H, m), 6.69 (2H, m), 6.88 (1 H, m), 7.07 (3H, m), 7.31 (1H, s); API MS(m/e)=389 [M+1].

Example 10

Synthesis of 2-[1,1'-Biphenyl]-4-yl-N-[5-(1,1-dioxo-1λ$^6$-isothiazolidin-2-yl)-1H-indazol-3-yl]acetamide (10)

The title compound was obtained in a yield of 40% according to the same procedure as Example 2, except that 1,1'-biphenylacetyl chloride was used instead of 3-chlorophenylacetyl chloride.

$^1$H NMR (CD$_3$OD, ppm): δ 2.45 (2H, m), 3.38 (2H, t), 3.73 (2H, t), 3.82 (2H, s), 7.30 (1H, t), 7.41 (4H, m), 7.48 (2H, d), 7.58 (6H, m); ESI MS(m/e)=447 [M+1].

Example 11

Synthesis of 2-(3-Bromophenyl)-N-[5-(1,1-dioxo-1λ$^6$-isothiazolidin-2-yl)-1 H-indazol-3-yl]acetamide (11)

The title compound was obtained in a yield of 50% according to the same procedure as Example 2, except that 3-bromophenylacetyl chloride was used instead of 3-chlorophenylacetyl chloride.

$^1$H NMR (CD$_3$OD, ppm): δ 2.47 (2H, m), 3.40 (2H, t), 3.76 (4H, m), 7.25 (1H, t), 7.35 (2H, m), 7.44 (2H, m), 7.59 (2H, d); ESI MS(m/e)=450 [M+1].

Example 12

Synthesis of 2-(4-Bromophenyl)-N-[5-(1,1-dioxo-1λ$^6$-isothiazolidin-2-yl)-1H-indazol-3-yl]acetamide (12)

The title compound was obtained in a yield of 46% according to the same procedure as Example 2, except that 4-bromophenylacetyl chloride was used instead of 3-chlorophenylacetyl chloride.

$^1$H NMR (CD$_3$OD, ppm): δ 2.48 (2H, m), 3.41 (2H, t), 3.75 (4H, m), 7.33 (2H, d), 7.44 (2H, s), 7.49 (dH, d), 7.56 (1H, s); ESI MS(m/e)=450 [M+1].

Example 13

Synthesis of N-[5-(1,1-Dioxo-1λ$^6$-isothiazolidin-2-yl)-1H-indazol-3-yl]-2-phenylethanethioamide(13)

100 mg (0.3 mmol) of the compound obtained in Example 1 was dissolved in tetrahydrofuran, and then 72 mg (0.18 mmol) of Lawesson's reagent(2,4-bis(4-methoxyphenyl)-1, 3-dithia-2,4-diphosphethane-2,4-disulfide) was added thereto. The mixture was heated under, reflux for 2 hours. The solvent was removed under reduced pressure, and the residue was then treated with ethyl acetate and hexane. The resulting precipitate was purified by silica gel column chromatography (eluent:methanol/dichloromethane=5/95(v/v)) to give 80 mg of the title compound in a yield of 69%.

API MS(m/e)=387 [M+1].

Example 14

Synthesis of N-[5-(1,1-Dioxo-1$\lambda^6$-isothiazolidin-2-yl)-1H-indazol-3-yl]-N'-hydroxy-2-phenylethaneimidoamide(14)

20 mg (0.052 mmol) of the compound obtained in Example 13 was dissolved in methanol, and then 9 mg (0.1 mmol) of sodium bicarbonate and 7 mg (0.1 mmol) of hydroxylamine hydrochloride salt were added thereto. The mixture was heated under reflux for 2 hours. The solvent was removed by evaporation under reduced pressure, and the residue was then purified by silica gel column chromatography (eluent:methanol/dichloromethane=5/95(v/v)) to give 4 mg of the title compound in a yield of 20%.

API MS(m/e)=386 [M+1].

Example 15

Synthesis of 2-(1,3-Benzodioxol-5-yl)-N-[5-(1,1-dioxo-1$\lambda^6$-isothiazolidin-2-yl)-1H-indazol-3-yl]acetamide(15)

The title compound was obtained in a yield of 36% according to the same procedure as Example 2, except that 1,3-benzodioxol-5-yl-acetyl chloride was used instead of 3-chlorophenylacetyl chloride.

$^1$H NMR (DMSO-d$_6$, ppm): δ 2.41 (2H, m), 3.42 (2H, t), 3.62 (2H, s), 3.68 (2H, t), 5.95 (2H, s), 6.82 (2H, s), 6.93 (1H, s), 7.34 (1H, d), 7.42 (1H, d), 7.58 (1H, s); ESI MS(m/e)=415 [M+1].

Example 16

Synthesis of N-[5-(1,1-Dioxo-1$\lambda^6$-isothiazolidin-2-yl)-1H-indazol-3-yl]-2-(1-naphthyl)acetamide(16)

The title compound was obtained in a yield of 60% according to the same procedure as Example 2, except that 1-naphthylacetyl chloride was used instead of 3-chlorophenylacetyl chloride.

$^1$H NMR (CD$_3$OD+CDCl$_3$, ppm): δ 2.47 (2H, m), 3.34 (2H, t), 3.69 (2H, t), 4.24 (2H, s), 7.35 (1H, d), 7.40 (1H, dd), 7.47 (2H, m), 7.55 (3H, m), 7.80 (1H, d), 7.85 (1H, d), 8.11 (1H, d); ESI MS(m/e)=421 [M+1].

Example 17

Synthesis of N-[5-(1,1-Dioxo-1$\lambda^6$-isothiazolidin-2-yl)-1H-indazol-3-yl]-2-(2-naphthyl)acetamide(17)

The title compound was obtained in a yield of 57% according to the same procedure as Example 2, except that 2-naphthylacetyl chloride was used instead of 3-chlorophenylacetyl chloride.

$^1$H NMR (CD$_3$OD+CDCl$_3$, ppm): δ 2.43 (2H, m), 3.33 (2H, t), 3.66 (2H, t), 3.92 (2H, s), 7.39 (4H, m), 7.49 (1H, d), 7.57 (1H, s), 7.79 (3H, m), 7.84 (1H, s); ESI MS(m/e)=421 [M+1].

Example 18

Synthesis of N-[5-(1,1-Dioxo-1$\lambda^6$-isothiazolidin-2-yl)-1H-indazol-3-yl]-2-(3-nitrophenyl)acetamide(18)

The title compound was obtained in a yield of 30% according to the same procedure as Example 2, except that 3-nitrophenylacetyl chloride was used instead of 3-chlorophenylacetyl chloride.

$^1$H NMR (CD$_3$OD+DMSO-d$_6$, ppm): δ 2.42 (2H, m), 3.41 (2H, t), 3.68 (2H, t), 3.91 (2H, s), 7.28 (1H, d), 7.34 (1H, d), 7.42 (1H, d), 7.62 (1H, s), 7.82 (1H, d), 8.12(1H, d), 8.29 (1H, s); ESI MS(m/e)=415 [M+1].

Example 19

Synthesis of N-[5-(1,1-Dioxo-1$\lambda^6$-isothiazolidin-2-yl)-1H-indazol-3-yl]acetamide(19)

The title compound was obtained in a yield of 70% according to the same procedure as Example 2, except that acetyl chloride was used instead of 3-chlorophenylacetyl chloride.

$^1$H NMR (DMSO-d$_6$, ppm): δ 2.44 (2H, m), 3.53 (2H, t), 3.77 (2H, t), 6.48 (1H, s), 7.49 (1H, dd), 7.72 (1H, d), 8.18 (1H, d); API MS(m/e)=295 [M+1].

Example 20

Synthesis of N-[5-(1,1-Dioxo-1$\lambda^6$-isothiazolidin-2-yl)-1H-indazol-3-yl]-2-[4-(methylsulfanil)phenyl]acetamide(20)

The title compound was obtained in a yield of 58% according to the same procedure as Example 2, except that 4-(methylsulfanil)phenylacetyl chloride was used instead of 3-chlorophenylacetyl chloride.

$^1$H NMR (CD$_3$OD+CDCl$_3$, ppm): δ 2.44 (3H, s), 2.51 (2H, m), 3.38 (2H, t), 3.72 (2H, s), 3.76 (2H, t), 7.22 (2H, d), 7.32 (2H, d), 7.40 (2H, m), 7.60 (1H, s); API MS(m/e)=417 [M+1].

Example 21

Synthesis of 2-(3-Aminophenyl)-N-[5-(1,1-dioxo-1$\lambda^6$-isothiazolidin-2-yl)-1H-indazol-3-yl]acetamide(21)

The procedure was carried out according to the same procedure as Preparation 1-4), except that the compound obtained in Example 18 was used instead of the compound obtained in Preparation 1-3). Then, the residue was purified by silica gel column chromatography(eluent:n-hexane/ethylacetate=1/4(v/v)) to give the title compound in a yield of 28%.

$^1$H NMR (DMSO-d$_6$, ppm): δ 2.39 (2H, m), 3.47 (2H, t), 3.54 (2H, s), 3.68 (2H, t), 5.11 (1H, s), 6.44 (1H, d), 6.52 (1H, d), 6.58 (1H, s), 6.96 (1H, t), 7.34(1H, d), 7.45 (1H, d), 7.57 (1H, s), 10.53 (1H, s); ESI MS(m/e)=386 [M+1].

Example 22

Synthesis of N-[5-(1,1-Dioxo-1$\lambda^6$-isothiazolidin-2-yl)-1H-indazol-3-yl]ethanethioamide(22)

The procedure was carried out according to the same procedure as Example 13, except that the compound obtained in Example 19 was used instead of the compound obtained in Example 1. Then, the residue was purified by silica gel column chromatography(eluent:n-hexane/ethylacetate=1/4(v/v)) to give the title compound in a yield of 34%.

ESI MS(m/e)=311 [M+1].

Example 23

Synthesis of N-[5-(1,1-Dioxo-1$\lambda^6$-isothiazolidin-2-yl)-1H-indazol-3-yl]-N'-hydroxyethaneimidoamide(23)

20 mg (0.05 mmol) of the compound obtained in Example 22 was dissolved in methanol, and then 9 mg(0.1 mmol) of sodium bicarbonate and 7 mg(0.1 mmol) of hydroxylamine hydrochloride were added thereto. The mixture was heated under reflux for 2 hours. The solvent was removed under reduced pressure, and then the residue was purified by silica gel column chromatography(eluent:methanol/dichloromethane=5/95(v/v)) to give 4 mg of the title compound in a yield of 20%.

ESI MS(m/e)=310 [M+1].

Example 24

Synthesis of 2-(3,4-Dichlorophenyl)-N-[5-(1,1-dioxo-1$\lambda^6$-isothiazolidin-2-yl)-1H-indazol-3-yl]acetamide(24)

The title compound was obtained in a yield of 67% according to the same procedure as Example 2, except that 3,4-dichlorophenylacetyl chloride was used instead of 3-chlorophenylacetyl chloride.

$^1$H NMR (DMSO-d$_6$, ppm): δ 2.39 (2H, p), 3.46 (2H, t), 3.68 (2H, t), 3.78 (2H, s), 7.36 (2H, m), 7.46 (1H, d), 7.56 (1H, m), 7.61 (1H, d), 7.65 (1H, s); ESI MS(m/e)=439 [M+1].

Example 25

Synthesis of N-[5-(1,1-Dioxo-1$\lambda^6$-isothiazolidin-2-yl)-1H-indazol-3-yl]-3-phenylpropanamide(25)

The title compound was obtained in a yield of 21% according to the same procedure as Example 2, except that 3-phenylpropanoyl chloride was used instead of 3-chlorophenylacetyl chloride.

$^1$H NMR (CD$_3$OD+CDCl$_3$, ppm): δ 2.50 (2H, m), 2.76 (2H, t), 3.04 (2H, t), 3.40 (2H, t), 3.76 (2H, t), 7.16 (1H, m), 7.26 (4H, d), 7.40 (2H, m), 7.53(1H, s); ESI MS(m/e)=385 [M+1].

Example 26

Synthesis of N-[5-(1,1-Dioxo-1$\lambda^6$-isothiazolidin-2-yl)-1H-indazol-3-yl]-2-(4-isopropylphenyl)acetamide(26)

The title compound was obtained in a yield of 32% according to the same procedure as Example 2, except that 4-isopropylphenylacetyl chloride was used instead of 3-chlorophenylacetyl chloride.

$^1$H NMR (CD$_3$OD+CDCl$_3$, ppm): δ 1.20 (6H, d), 2.44 (2H, m), 2.85 (1H, m), 3.41 (2H, t), 3.72 (4H, m), 7.17 (2H, d), 7.30 (3H, m), 7.38 (1H, dd), 7.64 (1H, s); ESI MS(m/e)=413 [M+1].

Example 27

Synthesis of N-[5-(1,1-Dioxo-1$\lambda^6$-isothiazolidin-2-yl)-1H-indazol-1-yl-2-(3-methylphenyl)acetamide (27)

The title compound was obtained in a yield of 67% according to the same procedure as Example 2, except that 3-methylphenylacetyl chloride was used instead of 3-chlorophenylacetyl chloride.

$^1$H NMR (CD$_3$OD+CDCl$_3$+DMSO-d$_6$, ppm): δ 2.30 (3H, s), 2.40 (2H, m), 3.45 (2H, t), 3.67 (4H, m), 7.20 (3H, m), 7.36 (2H, m), 7.45 (1H, d), 7.58 (1H, s); ESI MS(m/e)=4385 [M+1].

Example 28

Synthesis of N-[5-(1,1-Dioxo-1$\lambda^6$-isothiazolidin-2-yl)-1H-indazol-3-yl]-2-(4-methylphenyl)acetamide (28)

The title compound was obtained in a yield of 69% according to the same procedure as Example 2, except that 4-methylphenylacetyl chloride was used instead of 3-chlorophenylacetyl chloride.

$^1$H NMR (CD$_3$OD+CDCl$_3$+DMSO-d$_6$, ppm): δ 2.26 (3H, s), 2.40(2H, m), 3.38 (2H, t), 3.67 (4H, m), 7.10 (1H, d), 7.17 (1H, m), 7.27 (2H, m), 7.33 (1H, m), 7.40(1H, d), 7.57 (1H, s); ESI MS(m/e)=385 [M+1].

Example 29

Synthesis of N-[5-(1,1-Dioxo-1$\lambda^6$-isothiazolidin-2-yl)-1H-indazol-3-yl]-2-14-(methylsulfonyl)phenyl]acetamide(29)

100 mg (0.26 mmol) of the compound obtained in Example 1 was dissolved in tetrahydrofuran, and 100 mg (0.50 mmol) of 4-methylthiophenylacetyl chloride was then added thereto. The mixture was heated under reflux for 2 hours. The solvent was removed under reduced pressure, ethyl acetate was added thereto, and then the organic phase was washed with water. The solvent was removed under reduced pressure, the solid thus obtained was dissolved in dichloromethane, and then 60 mg(0.36 mmol) of m-chloroperbenzoic acid was added thereto. The mixture was stirred at room temperature for one hour. 10% sodium thiosulfate was added thereto, and then the mixture was further stirred for one hour. The organic phase was separated and washed with water. Dichloromethane was removed, and 10 ml of tetrahydrofuran and 3 ml of aqueous 2N sodium hydroxide solution were added to the solid. The mixture was stirred for 2 hours. The resultant was extracted with ethyl acetate, and then the extracted ethyl acetate solution was washed with water three times. The solvent was removed under reduced pressure, and then the residue was purified by silica gel column chromatography (eluent:methanol/dichloromethane=5/95(v/v)) to give 60 mg of the title compound in a yield of 51%.

$^1$H NMR (DMSO-d$_6$, ppm): δ 2.39 (2H, p), 3.21 (3H, s), 3.46 (2H, t), 3.68 (2H, t), 3.89 (2H, s), 7.34 (2H, dd), 7.46 (2H, d), 7.57 (2H, m), 7.65 (2H, d), 7.91(2H, d); API MS(m/e)=449 [M+1].

Example 30

Synthesis of N-[5-(1,1-Dioxo-1$\lambda^6$-isothiazolidin-2-yl)-1H-indazol-3-yl]-2-(4-methyl-1-piperazinyl)acetamide(30)

The procedure was carried out according to the same procedure as Example 2, except that 2-bromoacetyl bromide was used instead of 3-chlorophenylacetyl chloride. Then, N,N-dimethylformamide was added thereto to form a solution. Anhydrous potassium carbonate and 4-methylpiperazine were added to the solution. The mixture was stirred for 2 hours. The solvent was removed by evaporation under reduced pressure, and then the residue was purified by silica gel column chromatography (eluent:methanol/dichloromethane=5:95(v/v)) to give the title compound in a yield of 21%.

$^1$H NMR (CD$_3$OD, ppm): δ 2.48 (5H, m), 2.82 (8H, br s), 3.34 (2H, s), 3.42 (2H, t), 3.80 (2H, t), 7.46 (2H, m), 7.72 (1H, s); API MS(m/e)=393 [M+1].

Example 31

Synthesis of N-[5-(1,1-Dioxo-1$\lambda^6$-isothiazolidin-2-yl)-1H-indazol-3-yl]-2-(4-morpholinyl)acetamide (31)

The title compound was obtained in a yield of 31% according to the same procedure as Example 30, except that morpholine was used instead of 4-methylpiperazine.

¹H NMR (CD₃OD, ppm): δ 2.48 (2H, m), 2.64 (4H, br s), 3.41 (2H, t), 3.77(8H, m), 7.45 (2H, m), 7.71 (1H, s); API MS(m/e)=380 [M+1].

Example 32

Synthesis of N-[5-(1,1-Dioxo-1λ⁶-isothiazolidin-2-yl)-1H-indazol-3-yl]-2-(1-piperidinyl)acetamide(32)

The title compound was obtained in a yield of 33% according to the same procedure as Example 30, except that piperidine was used instead of 4-methylpiperazine.

¹H NMR (CD₃OD+CDCl₃, ppm): δ 1.45 (2H, br s), 1.68 (4H, m), 2.52 (2H, m), 2.61 (4H, br s), 3.20 (2H, s), 3.41 (2H, t), 3.81 (2H, t), 7.45 (2H, m), 7.77(1H, s); ESI MS(m/e)=378 [M+1].

Example 33

Synthesis of N-[5-(1,1-Dioxo-1λ⁶-isothiazolidin-2-yl)-1H-indazol-3-yl]-2-[4-(4-pyridinyl)phenyl]acetamide(33)

150 mg (0.373 mmol) of the compound obtained in Preparation 1 was dissolved in 10 ml of tetrahydrofuran, and then 100 mg (0.373 mmol) of 4-pyridinylphenylacetyl chloride was added thereto. The mixture was heated under reflux for 2 hours. After the solvent was removed under reduced pressure, the residue was treated with ethyl acetate and water to give 16 mg of the title compound as a solid in a yield of 10%.

¹H NMR (DMSO-d₆, ppm): δ 2.38 (2H, m), 3.45 (2H, t), 3.67 (2H, t), 3.81 (2H, s), 7.35 (1H, d), 7.46 (2H, d), 7.56 (3H, m), 7.72 (2H, d), 7.80 (2H, d), 8.63 (3H, d), 10.69 (1H, s); API MS(m/e)=448 [M+1].

Example 34

Synthesis of N-[5-(1,1-Dioxo-1λ⁶-isothiazolidin-2-yl)-1H-indazol-3-yl]-2-[4-(4-piperidinyl)phenyl]acetamide(34)

130 mg (0.337 mmol) of the compound obtained in Preparation 1 was added to 10 ml of tetrahydrofuran, and then 109 mg (0.502 mmol) of 4-nitrophenylacetyl chloride was added thereto. The mixture was heated under reflux for 2 hours. The solvent was removed under reduced pressure, and then the residue was purified by silica gel column chromatography (eluent:hexane/ethylacetate=1:4(v/v)) to give 30 mg of the title compound in a yield of 20%.

¹H NMR (CDCl₃+CD₃OD, ppm): δ 1.55(2H, m), 1.69 (4H, m), 2.51 (2H, m), 3.09 (4H, m), 3.38 (2H, t), 3.70 (2H, s), 3.78 (2H, t), 6.95 (2H, d), 7.26 (2H, m), 7.63 (1H, s); API MS(m/e)=454 [M+1].

Example 35

Synthesis of N-[5-(1,1-Dioxo-1λ⁶-isothiazolidin-2-yl)-1H-indazol-3-yl]-2-[4-(4-morpholinyl)phenyl]acetamide(35)

35-1) Synthesis of Ethyl 2-[4-(4-Morpholinyl)phenyl]-2-oxoacetate 0.25 g (1.53 mmol) of 4-phenylmorpholine was dissolved in 20 ml of dichloromethane, was added 0.19 ml(1.68 mmol) of diethyloxalyl chloride at −10° C. 3.4 ml (3.37 mmol) of 1.0 M titanium chloride solution(in dichloromethane) was added dropwise at −10° C., and then the mixture was stirred for 4 hours while keeping the temperature at −10° C. The mixture was poured into ice water, and then extracted with diethyl ether three times. The resulting product was concentrated under reduced pressure, and then purified by silica gel column chromatography (eluent:hexane/ethylacetate=2/1 (v/v)) to give 0.15 mg of the title compound in a yield of 38%.

¹H NMR (CDCl₃ ppm): δ 1.40 (3H, t), 3.37 (4H, t), 3.84 (4H, t), 4.41 (2H, q), 6.85 (2H, d), 7.92 (2H, d);

35-2) Synthesis of Ethyl 2-[4-(4-Morpholinyl)phenyl]acetate 0.5 g (1.901 mmol) of the compound obtained in Example 35-1) was added to a solvent mixture (dioxane/water=10 ml/0.5 ml), and then 1.007 g (9.505 mmol) of sodium hypophosphite hydrate and 0.05 g of palladium-adsorbed activated carbon(10%) were added thereto. The mixture was heated under reflux for 5 hours, and then cooled to room temperature. Additional 1.007 g (9.505 mmol) of sodium hypophosphite hydrate and 0.05 g of palladium-adsorbed activated carbon(10%) were added to the mixture. The mixture was stirred for another 5 hours. The resulting suspension was filtered through celite, and the solvent was removed under reduced pressure. The residue was purified by silica gel column chromatography (eluent:hexane/ethylacetate=2:1(v/v)) to give 0.37 g of the title compound in a yield of 78%.

¹H NMR (CDCl₃+CD₃OD, ppm): δ 1.25 (3H, t), 3.14 (4H, m), 3.52 (2H, s), 3.85 (4H, m), 4.14 (2H, m), 6.88 (2H, d), 7.18 (2H, d);

35-3) Synthesis of 2-[4-(4-Morpholinyl)phenyl]acetyl Chloride 0.35 g (1.41 mmol) of the compound obtained in Example 35-2) was dissolved in 12 ml of tetrahydrofuran, and then 0.18 g (4.23 mmol) of lithium hydroxide in 4 ml of water was added thereto. The mixture was stirred for 12 hours. The solvent was removed under reduced pressure. The residue was dissolved in 15 ml of dichloromethane, and then 5 molar equivalents of thionyl chloride was added thereto. The mixture was stirred at room temperature for 4 hours. The solvent was removed by evaporation under reduced pressure to give 0.44 g of the title compound. The compound was used for subsequent reactions without further purification processes.

35-4) Synthesis of N-[5-(1,1-Dioxo-1λ⁶-isothiazolidin-2-yl)-1H-indazol-3-yl]-2-[4-(4-morpholinyl)phenyl]acetamide 0.2 g (0.518 mmol) of the compound obtained in Preparation 1 was added in 40 ml of tetrahydrofuran, and then 0.316 g (1.2 mmol) of 4-morpholinylphenylacetyl chloride was added thereto. The mixture was heated under reflux for 7 hours. Subsequently, the solvent was removed under reduced pressure. The residue was purified by silica gel column chromatography (eluent:dichloromethane/methanol=19:1 (v/v)) to give 10 mg of the title compound in a yield of 4%.

¹H NMR (CDCl₃+CD₃OD, ppm): δ 2.47 (2H, m), 3.10 (4H, m), 3.34 (2H, t), 3.67 (2H, s), 3.75 (2H, t), 3.81 (4H, 4H), 6.87 (2H, d), 7.25 (2H, d), 7.31(1H, d), 7.39 (1H, d), 7.67 (1H, s); API MS(m/e)=456 [M+1].

Example 36

Synthesis of N-[5-(1,1-Dioxo-1λ⁶-isothiazolidin-2-yl)-1H-indazol-3-yl]-2-[4-(3-thienyl)phenyl]acetamide(36)

106 mg (0.28 mmol) of the compound obtained in Preparation 1 was added to 10 ml of tetrahydrofuran, and then 97 mg (0.41 mmol) of 4-(3-thienyl)phenylacetyl chloride was added thereto. The mixture was heated under reflux for 2 hours. After the resulting mixture was cooled to room temperature, 5 ml of aqueous 1N sodium hydroxide solution thereto. The mixture was stirred for 2 hours. The resultant was extracted with ethyl acetate, and then washed with water three times. The solvent was removed under reduced pressure, and the residue was then treated with methanol to give 51 mg of the title compound in a yield of 41%.

$^1$H NMR (DMSO-$d_6$, ppm): δ 2.37 (2H, m), 3.45 (2H, t), 3.66 (2H, t), 3.74 (2H, s), 7.35 (1H, d) 7.43 (2H, d), 7.46 (1H, d), 7.54 (1H, d), 7.56 (1H, d), 7.63 (1H, dd), 7.70 (2H, d), 7.85 (1H, s), 10.63 (1H, s); ESI MS(m/e)=453 [M+1].

Example 37

Synthesis of N-[5-(1,1-Dioxo-1λ$^6$-isothiazolidin-2-yl)-1H-indazol-3-yl]-2-[4-(4-morpholinylsulfonyl)phenyl]acetamide(38)

81 mg (0.21 mmol) of the compound obtained in Preparation 1 was added to 10 ml of tetrahydrofuran, and then 91 mg (0.32 mmol) of 4-(4-morpholinylsulfonyl)phenylacetyl chloride was added thereto. The mixture was heated under reflux for 2 hours. After the resulting mixture was cooled to room temperature, 5 ml of aqueous 1N sodium hydroxide solution thereto. The mixture was stirred for 2 hours. The resultant was extracted with ethyl acetate, and then washed with water three times. The solvent was removed under reduced pressure, and the residue was then treated with diethyl ether to give 69 mg of the title compound in a yield of 63%.

$^1$H NMR (DMSO-$d_6$, ppm): δ 2,39 (2H, m), 2,87 (4H, br), 3.45 (2H, t), 3.62 (4H, br), 3.68 (2H, t), 3.90 (2H, s), 7.35 (1H, d), 7.47 (1H, d), 7.56 (1H, s), 7.67 (2H, d), 7.73 (2H, d), 10.73 (1H, s); ESI MS(m/e)=520 [M+1].

Example 38

Synthesis of N-[5-(1,1-Dioxo-1λ$^6$-isothiazolidin-2-yl)-1H-indazol-3-yl]-2-(4-methoxyphenyl)acetamide (37)

60 mg of the title compound was obtained in a yield of 58% according to the same procedure as Example 2, except that 4-methoxyphenylacetyl chloride was used instead of 3-chlorophenylacetyl chloride.

$^1$H NMR (DMSO-$d_6$OD, ppm): δ 2.39 (2H, m), 3.46 (2H, t), 3.68 (4H, m), 3.74 (3H, s), 6.91 (2H, d), 7.31 (3H, m), 7.45 (1H, d), 7.55 (1H, s); API MS(m/e)=401 [M+1].

Example 39

Synthesis of N-[5-(1,1-Dioxo-1λ$^6$-isothiazolidin-2-yl)-1H-indazol-3-yl]-2-[4-(2-furyl)phenyl]acetamide (39)

24 mg (0.06 mmol) of the compound obtained in Preparation 1 was added to 10 ml of tetrahydrofuran, and then 21 mg (0.09 mmol) of 4-(2-furyl)phenylacetyl chloride was added thereto. The mixture was heated under reflux for 2 hours. After the resulting mixture was cooled to room temperature, 5 ml of aqueous 1N sodium hydroxide solution thereto. The mixture was stirred for 2 hours. The resultant was extracted with ethyl acetate, and then washed with water three times. The solvent was removed under reduced pressure, and the residue was then treated with dichloromethane to give 13 mg of the title compound in a yield of 48%.

$^1$H NMR (DMSO-$d_6$, ppm): δ 2,38 (2H, m), 3.45 (2H, t), 3.69 (2H, t), 3.75 (2H, s), 6.58 (1H, s), 6.91 (1H, s), 7.35 (1H, d), 7.45 (3H, m), 7.55 (1H, s), 7.68 (2H, d), 7.73 (1H, s), 10.63 (1H, s); ESI MS(m/e)=437 [M+1].

Example 40

Synthesis of N-[5-(1,1-Dioxo-1λ$^6$-isothiazolidin-2-yl)-1H-indazol-3-yl]-2-4-[(4-methyl-1-piperazinyl)sulfonyl]phenylacetamide(40)

69 mg (0.178 mmol) of the compound obtained in Preparation 1 was added to 10 ml of tetrahydrofuran, and then 112 mg (0.355 mmol) of 4-[(4-methyl-1-piperazinyl)sulfonyl]phenylacetyl chloride was added thereto. The mixture was heated under reflux for 2 hours. After the resulting mixture was cooled to room temperature, 5 ml of aqueous 1N sodium hydroxide solution thereto. The mixture was stirred for 2 hours. The resultant was extracted with ethyl acetate, and then washed with water three times. The solvent was removed under reduced pressure, and the residue was then purified by silica gel column chromatography (eluent:dichloromethane/methanol=9/1 (v/v)) to give 12 mg of the title compound in a yield of 13%.

$^1$H NMR (CDCl$_3$, ppm): δ 2.26 (3H, s), 2.48 (4H, br), 2.51 (2H, m), 3.08 (4H, br), 3.39 (2H, t), 3.47 (2H, s), 3.79 (2H, t), 7.30 (1H, d), 7.43 (1H, d), 7.80(2H, d), 7.90 (1H, s), 8.43 (2H, d), 8.72 (1H, s); ESI MS(m/e)=533 [M+1].

Example 41

Synthesis of 2-(1H-Benzimidazol-1-yl)-N-[5-(1,1-dioxo-1λ$^6$-isothiazolidin-2-yl)-1H-indazol-3-yl]acetamide(41)

41-1) Synthesis of Benzyl 3[(2-Bromoacetyl)amino]-5-(1,1-dioxo-1λ$^6$-isothiazolidin-2-yl)-1H-indazol-1-carboxylate 0.5 g (1.404 mmol) of the compound obtained in Preparation 1 was added to 25 ml of tetrahydrofuran, and then 0.147 ml (1.2 eq) of bromoacetyl bromide was added thereto. The mixture was heated under reflux for one hour. After the solvent was removed by evaporation under reduced pressure, the residue was purified by silica gel column chromatography (eluent:ethylacetate/hexane=4/1(v/v)) to give 0.47 g of the title compound in a yield of 66%.

1H NMR (CDCl$_3$+CD$_3$OD, ppm): δ 2.53 (2H, m), 3.42 (2H, t), 3.82 (2H, t), 4.04 (2H, s), 5.47 (2H, s), 7.34 (3H, m), 7.45 (2H, m), 7.57 (1H, dd), 7.79 (1H, s), 8.00 (1H, s).

41-2) Synthesis of 2-(1H-Benzimidazol-1-yl)-N-[5-(1,1-dioxo-1λ$^6$-isothiazolidin-2-yl)-1H-indazol-3-yl]acetamide 20 mg (0.169 mmol) of benzimidazole was dissolved in 10 ml of N,N-dimethylformamide, and then 20 mg (0.5 mmol) of sodium hydride was added thereto. After 5 minutes, 70 mg (0.38 mmol) of the compound in Example 41-1 was added thereto. The mixture was stirred for one hour. The solvent was removed under reduced pressure, and the residue was then treated with ethyl acetate to give 20 mg of the title compound in a yield of 35%.

$^1$H NMR (DMSO-$d_6$OD, ppm): δ 2.36 (2H, m), 3.44 (2H, t), 5.29 (2H, s), 7.25 (2H, m), 7.35 (1H, d), 7.48 (1H, d), 7.59 (2H, m), 7.70 (1H, d), 8.28 (1H, s); ESI MS(m/e)=411 [M+1].

Example 42

Synthesis of N-[5-(1,1-Dioxo-1λ$^6$-isothiazolidin-2-yl)-1H-indazol-3-yl]-2-(4-ethoxyphenyl)acetamide (42)

22 mg of the title compound was obtained in a yield of 41% according to the same procedure as Example 2, except that 4-ethoxyphenylacetyl chloride was used instead of 3-chlorophenylacetyl chloride.

$^1$H NMR (DMSO-d$_6$OD, ppm): δ 1.32 (3H, t), 2.40 (2H, m), 3.46 (2H, t), 3.67 (4H, m), 4.01 (2H, m), 6.90 (2H, d), 7.30 (3H, m), 7.45 (1H, d), 7.55 (1H, s), 10.53 (1H, s); API MS(m/e)=413 [M+1].

Example 43

Synthesis of N-[5-(1,1-Dioxo-1λ$^6$-isothiazolidin-2-yl)-1H-indazol-3-yl]-2-[4-(4-morpholinylmethyl)phenyl]acetamide(43)

1 g (2.591 mmol) of the compound obtained in Preparation 1 was added to 80ml of tetrahydrofuran, and then 0.8 g (1.2 eq) of 4-(bromomethyl)phenylacetyl bromide was added thereto. The mixture was heated under reflux for 2 hours. The solvent was removed under reduced pressure, and the residue was then purified by silica gel column chromatography (eluent:hexane/ethylacetate=1/4(v/v)) to give 0.9 g of the title compound in a yield of 58%.

0.1 g (0.168 mmol) of the compound thus obtained was dissolved in 15 ml of N,N-dimethylformamide, and then 0.03 ml (2.0 eq) of morpholine and 50 mg (2.0 eq) of anhydrous potassium carbonate were added thereto. The mixture was stirreat at 60° C. for 2 hours. The solvent was removed under reduced pressure, and the residue was then purified by silica gel column chromatography (eluent:dichloromethane/methanol=19/1(v/v)) to give 55 mg of the title compound in a yield of 65%.

$^1$H NMR (DMSO-d$_6$OD, ppm): δ 2.34 (4H, br s), 2.39 (2H, m), 3.46 (4H, m), 3.57 (4H, m), 3.73 (4H, m) 7.27 (2H, d), 7.34 (2H, m), 7.36 (3H, m), 7.46(1H, d), 7.57 (1H, s); API MS(m/e)=456 [M+1].

Example 44

Synthesis of N-[5-(1,1-Dioxo-1λ$^6$-isothiazolidin-2-yl)-1H-indazol-3-yl]-2-4-[(4-methyl-1-piperazinyl)methyl]phenylacetamide(44)

44 mg of the title compound was obtained in a yield of 54% according to the same procedure as Example 43, except that 4-methylpiperazine was used instead of morpholine.

$^1$H NMR (CDCl$_3$+CD$_3$OD, ppm): δ 1.99 (3H, s), 2.24 (8H, m), 3.04 (2H, m), 3.11 (2H, t), 3.22 (2H, s), 3.51 (4H, m), 7.01 (2H, d), 7.11 (4H, m), 7.40 (1H, s); ESI MS(m/e)=482 [M+1].

Example 45

Synthesis of N-[5-(1,1-Dioxo-1λ$^6$-isothiazolidin-2-yl)-1H-indazol-3-yl]-2-(4-nitrophenyl)acetamide(45)

386 mg (1.0 mmol) of the compound obtained in Preparation 1 was added to 10 ml of tetrahydrofuran, and 299 mg (1.5 mmol) of 4-nitrophenylacetyl chloride was added thereto. The mixture was heated under reflux for 2 hours. After the mixture was cooled to room temperature, 5 ml of aqueous 1N sodium hydroxide solution was added thereto. The mixture was stirred for 2 hours. The resultant was extracted with ethyl acetate, and then the extracted ethyl acetate solution was washed with water three times. After the solvent was removed under reduced pressure, the residue was treated with methanol to give 151 mg of the title compound as a solid in a yield of 36%.

$^1$H NMR (DMSO-d$_6$, ppm): δ 2.39 (2H, m), 3.54 (2H, t), 3.68 (2H, t), 3.93 (2H, s), 7.34 (1H, d), 7.47 (1H, d), 7.57 (1H, s), 7.67 (2H, d), 8.22 (2H, d), 10.72 (1H, s); ESI MS(m/e)=416 [M+1].

Example 46

Synthesis of N-[5-(1,1-Dioxo-1λ$^6$-isothiazolidin-2-yl)-1H-indazol-3-yl]-2-[4-(1H-imidazol-1-ylmethyl)phenyl]acetamide(46)

50 mg of the title compound was obtained in a yield of 66% according to the same procedure as Example 43, except that imidazole was used instead of morpholine.

$^1$H NMR (CDCD3+CD$_3$OD, ppm): δ 2.28 (2H, m), 3.05 (2H, s), 3.16 (2H, t), 3.53 (4H, m), 6.70 (2H, d), 6.89 (2H, d), 7.12 (2H, m), 7.22 (2H, d) 7.55 (1H, s), 7.79 (1H, d); ESI MS(m/e)=451 [M+1].

Example 47

Synthesis of N-[5-(1,1-Dioxo-1λ$^6$-isothiazolidin-2-yl)-1H-indazol-3-yl]-2-(4-phenyl-1H-imidazol-1-yl)acetamide(47)

10 mg of the title compound was obtained in a yield of 17% according to the same procedure as Example 41, except that 4-phenylimidazole was used instead of benzimidazole.

$^1$H NMR (CDCl$_3$+CD$_3$OD, ppm): δ 2.25 (2H, m), 3.13 (2H, t), 3.53 (2H, t), 4.71 (2H, s), 7.00 (1H, m), 7.11 (2H, m), 7.19 (3H, m), 7.46 (4H, m); ESI MS(m/e)=437 [M+1].

Example 48

Synthesis of N-[5-(1,1-Dioxo-1λ$^6$-isothiazolidin-2-yl)-1H-indazol-3-yl]-2-(4-phenyl-1-piperazinyl)acetamide(48)

20 mg of the title compound was obtained in a yield of 32% according to the same procedure as Example 41, except that 4-phenylpiperazine was used instead of benzimidazole.

$^1$H NMR (CDCl$_3$+CD$_3$OD+DMSO-d$_6$, ppm): δ 2.42 (2H, m), 2.74 (4H, m), 3.21 (4H, m), 3.38 (2H, t), 3.72 (4H, m), 6.75 (1H, t), 6.90 (2H, d), 7.17 (2H, m) 7.37 (2H, dd), 7.42 (1H, d), 7.67 (1H, s); ESI MS(m/e)=456 [M+1].

Example 49

Synthesis of 2-[3,4-Dihydro-2(1H)-isoquinolinyl]-N-[5-(1,1-dioxo-1λ$^6$-isothiazolidin-2-yl)-1H-indazol-3-yl]acetamide(49)

57 mg of the title compound was obtained in a yield of 68% according to the same procedure as Example 41, except that 3,4-dihydro-2(1H)-isoquinoline was used instead of benzimidazole.

$^1$H NMR (CDCl$_3$+CD$_3$OD, ppm): δ 2.56 (2H, m), 3.03 (4H, m), 3.43 (4H, m), 3.85 (4H, m), 7.08 (4H, m), 7.45 (2H, m), 7.83 (1H, s); ESI MS(m/e)=426 [M+1].

Example 50

Synthesis of N-[5-(1,1-Dioxo-1λ$^6$-isothiazolidin-2-yl)-1H-indazol-3-yl]-2-[4-(4-chlorophenyl)-1-piperazinyl]acetamide(50)

20 mg of the title compound was obtained in a yield of 41% according to the same procedure as Example 41, except that 4-(4-chlorophenyl)piperazine was used instead of benzimidazole.

$^1$H NMR (CDCl$_3$+CD$_3$OD, ppm): δ 2.55 (2H, m), 2.86 (4H, m), 3.36 (6H, m), 3.44 (2H, t), 3.87 (2H, t) 6.87 (3H, m), 7.19 (1H, t), 7.47 (2H, m), 7.82 (1H, s); ESI MS(m/e)=490 [M+1].

Example 51

Synthesis of N-[5-(1,1-Dioxo-1λ⁶-isothiazolidin-2-yl)-1H-indazol-3-yl]-2-[4-(4-methoxyphenyl)-1-piperazinyl]acetamide(51)

25 mg of the title compound was obtained in a yield of 53% according to the same procedure as Example 41, except that 4-(4-methoxyphenyl)piperazine was used instead of benzimidazole.

$^1$H NMR (CDCl$_3$+CD$_3$OD, ppm): δ 2.56 (2H, m), 3.44 (10H, m), 3.83 (5H, m), 4.16 (2H, s), 6.92 (4H, m), 7.46 (2H, m), 7.85 (1H, s); ESI MS(m/e)=485 [M+1].

Example 52

Synthesis of N-[5-(1,1-Dioxo-1λ⁶-isothiazolidin-2-yl)-1H-indazol-3-yl]-2-[4-(2-ethoxyphenyl)-1-piperazinyl]acetamide(52)

15 mg of the title compound was obtained in a yield of 20% according to the same procedure as Example 41, except that 4-(2-ethoxyphenyl)piperazine was used instead of benzimidazole.

$^1$H NMR (CDCl$_3$+CD$_3$OD, ppm): δ 1.48 (3H, t), 2.56 (2H, m), 2.91 (4H, m), 3.22 (4H, m), 3.34 (2H, m), 3.43 (2H, t), 3.85 (2H, t), 4.11 (2H, m), 7.00 (4H, m), 7.45 (2H, m), 7.85 (1H, s); API MS(m/e)=499 [M+1].

Example 53

Synthesis of 2-[4-(4-Acetylphenyl)-1-piperazinyl]-N-[5-(1,1-dioxo-1λ⁶-isothiazolidin-2-yl)-1H-indazol-3-yl]acetamide(53)

25 mg of the title compound was obtained in a yield of 51% according to the same procedure as Example 41, except that 4-(4-acetylphenyl)piperazine was used instead of benzimidazole.

$^1$H NMR (CDCl$_3$+CD$_3$OD, ppm): δ 2.55 (4H, m), 2.86 (2H, m), 3.43 (8H, m), 3.84 (2H, t), 4.06 (3H, s), 6.93 (2H, m), 7.46 (2H, m), 7.86 (1H, s), 7.90 (2H, m); API MS(m/e)=498 [M+1].

Example 54

Synthesis of N-[5-(1,1-Dioxo-1λ⁶-isothiazolidin-2-yl)-1H-indazol-3-yl]-2-(4-phenoxyphenyl)acetamide (54)

25 mg of the title compound was obtained in a yield of 30% according to the same procedure as Example 2, except that (4-phenoxyphenyl)acetyl chloride was used instead of 3-chlorophenylacetyl chloride.

$^1$H NMR (CDCl$_3$+CD$_3$OD, ppm): δ 2.44 (2H, m), 3.39 (2H, t), 3.72 (4H, m), 7.02 (5H, m), 7.34 (6H, m), 7.68 (1H, s); ESI MS(m/e)=463 [M+1].

Example 55

Synthesis of N-[5-(1,1-Dioxo-1λ⁶-isothiazolidin-2-yl)-1H-indazol-3-yl]-1-phenylcyclopentanecarboxamide(55)

24 mg of the title compound was obtained in a yield of 31% according to the same procedure as Example 2, except that 1-phenylcyclopentanecarbonyl chloride was used instead of 3-chlorophenylacetyl chloride.

$^1$H NMR (CDCl$_3$+CD$_3$OD, ppm): δ 1.74 (4H, m), 2.04 (2H, m), 2.49 (4H, m), 3.38 (2H, t), 3.68 (2H, t), 7.20 (5H, m), 7.38 (2H, m), 7.48 (1H, s); ESI MS(m/e)=425 [M+1].

Example 56

Synthesis of 2-Cyclopentyl-N-[5-(1,1-dioxo-1λ⁶-isothiazolidin-2-yl)-1H-indazol-3-yl]-2-phenylacetamide(56)

30 mg of the title compound was obtained in a yield of 38% according to the same procedure as Example 2, except that 2-cyclopentyl-2-phenylacetyl chloride was used instead of 3-chlorophenylacetyl chloride.

$^1$H NMR (CDCl$_3$+CD$_3$OD, ppm): δ 1.61 (6H, m), 2.11 (1H, m), 2.51 (2H, m), 2.79 (1H, m), 3.45 (4H, m), 3.78 (2H, t), 7.32 (5H, m), 7.54 (2H, m), (1H, s); ESI MS(m/e)=439 [M+1].

Example 57

Synthesis of N-[5-(1,1-Dioxo-1λ⁶-isothiazolidin-2-yl)-1H-indazol-3-yl]-2-phenylbutanamide(57)

35 mg of the title compound was obtained in a yield of 48% according to the same procedure as Example 2, except that 2-phenylbutanoyl chloride was used instead of 3-chlorophenylacetyl chloride.

$^1$H NMR (CDCl$_3$+CD$_3$OD, ppm): δ 0.94 (3H, t), 1.84 (1H, m), 2.17 (1H, m), 2.46 (2H, m), 3.34 (2H, t), 3.57 (1H, t), 3.72 (2H, t), 7.23 (5H, m), 7.38(2H, m), 7.56 (1H, s); ESI MS(m/e)=399 [M+1].

Example 58

Synthesis of t-Butyl 4-(2-[5-(1,1-Dioxo-1λ⁶-isothiazolidin-2-yl)-1H-indazol-3-yl]amino-2-oxoethyl)-1,3-thiazol-2-ylcarbamate(58)

58-1) Synthesis of t-Butyl 4-2-[(5-Nitro-1H-indazol-3-yl)amino]-2-oxoethyl-1,3-thiazol-2-ylcarbamate 2.0 g (10.204 mmol) of amino-N-hydroxy-5-nitrobenzenecarboxyimidoamide was dissolved in 120 ml of tetrahydrofuran, and then 0.82 g (60%, 2.0 eq) of sodium hydride was added thereto. After stirring 5 minutes at room temperature, was added 3.5 g (1.2 eq) of ethyl 2-2-[(t-butyloxycarbonyl)amino]-1,3-thiazol-4-ylacetate and stirred for one hour. After addition of 20 ml of N,N-dimethylformamide, further stirred under slight heating for 4 hours. The solvent was removed under reduced pressure, and the residue was then treated with ethyl acetate and water. The resulting precipitate was filtered and washed with water and diethyl ether to give 1.9 g of the title compound in a yield of 42%.

58-2) Synthesis of t-Butyl 4-2-[(5-Amino-1H-indazol-3-yl)amino]-2-oxoethyl-1,3-thiazol-2-ylcarbamate 1.9 g (4.24 mmol) of the compound obtained in Preparation 58-1) was dissolved in methanol, and palladium-adsorbed activated carbon(10%) was added thereto. The mixture was stirred under hydrogen atmosphere for 2 hours. The resulting suspension was filtered through celite, and then the filtrate was concentrated and dried to give 1.7 g of the title compound in a yield of 96%.

58-3) Synthesis of t-Butyl 4-2-[(5-[(3-Chloropropyl)sulfonyl]amino-1H-indazol-3-yl)amino]-2-oxoethyl-1,3-thiazol-2-ylcarbamate 1.7 g (4.07 mmol) of the compound obtained in Preparation 58-2) was dissolved in 100 ml of dichloromethane, and 1.53 ml (5.0 eq) of pyridine and 0.49 ml (1.0 eq) of 3-chloropropanesulfonyl chloride were added thereto. The mixture was stirred at room temperature for 2 hours. After the solvent was removed under reduced pressure, the residue was treated with ethyl acetate and water to give 0.8 g of the title compound as a solid in a yield of 37%.

$^1$H NMR (CDCl$_3$+CD$_3$OD, ppm): δ 1.35 (9H, s), 2.07 (2H, m), 3.02 (2H, t), 3.45 (2H, t), 3.69 (2H, s), 6.60 (1H, s), 7.20 (2H, m), 7.60 (1H, s); API MS(m/e)=529 [M+1].

58-4) Synthesis of t-Butyl 4-(2-[5-(1,1-Dioxo-1λ$^6$-isothiazolidin-2-yl)-1H-indazol-3-yl]amino-2-oxoethyl)-1,3-thiazol-2-ylcarbamate 0.7 g (1.33 mmol) of the compound obtained in Preparation 58-3) was dissolved in 50 ml of N,N-dimethylformamide, and 0.16 g (3.0 eq) of sodium hydride was added thereto. The mixture was stirred for 3 hours. The solvent was removed under reduced pressure, and then the residue was purified by silica gel column chromatography (eluent:n-hexane/ethyl acetate=1/4(v/v)) to give 0.1 g of the title compound in a yield of 15%.

$^1$H NMR (CD$_3$OD, ppm): δ 1.53 (9H, s), 2.49 (2H, m), 3.42 (2H, t), 3.80 (4H, m), 6.90 (1H, s), 7.44 (2H, m), 7.67 (1H, s); API MS(m/e)=493 [M+1].

Example 59

Synthesis of N-[5-(1,1-Dioxo-1λ$^6$-isothiazolidin-2-yl)-1H-indazol-3-yl]-2-4-[2-(2-ethoxyethoxy)ethoxy]phenylacetamide(59)

59-1) Synthesis of 2-(2-Ethoxyethoxy)ethyl 4-Methylbenzenesulfonate 432 mg (3.22 mmol) of 2-(2-ethoxyethoxy)ethanol was dissolved in 40 ml of dichloromethane, and 0.6 ml (4.19 mmol) of triethylamine and 614 mg (3.22 mmol) of p-toluenesulfonyl chloride were added thereto. The mixture was stirred at room temperature for 15 hours. After the solvent was removed under reduced pressure, 40 ml of water was added thereto. The mixture was extracted with 30 ml of ethyl acetate. The solvent was removed under reduced pressure to give 760 mg (2.64 mmol) of the title compound in a yield of 82%.

$^1$H NMR (CDCl$_3$, ppm): δ 1.20 (3H, t), 2.35 (3H, s), 3.35 (2H, q), 3.52 (2H, t), 3.57–3.60 (4H, m), 4.08 (2H, t), 7.33 (2H, d), 7.78 (2H, d); FAB MS(m/e)=289 [M+1].

59-2) Synthesis of 2-4-[2-(2-Ethoxyethoxy)ethoxy]phenylacetic Acid 281 mg (0.97 mmol) of the compound obtained in Example 59-1) and 162 mg (0.971 mmol) of 4-hydroxyphenylacetic acid methyl ester were dissolved in 30 ml of N,N-dimethylformamide, and then 58 mg (1.44mmol) of sodium hydride(60%) was added thereto. The mixture was stirred at room temperature for one hour. After the reaction was completed, 3 ml of methanol was added thereto. The solvent was removed under reduced pressure, and 40 ml of water was added thereto. The mixture was extracted with 30 ml of ethyl acetate. The solvent was removed under reduced pressure, and the residue was then purified by silica gel column chromatography to give 64 mg (0.239 mmol) of the title compound in a yield of 24%.

$^1$H NMR (CDCl$_3$, ppm): δ 1.21 (3H, t), 3.34 (2H, q), 3.51 (2H, t), 3.57–3.61 (4H, m), 3.82 (2H, s), 4.06 (2H, t), 6.86 (2H, d), 7.17 (2H, d); FAB MS(m/e)=269 [M+1].

59-3) Synthesis of N-[5-(1,1-Dioxo-1λ$^6$-isothiazolidin-2-yl)-1H-indazol-3-yl]-2-4-[2-(2-ethoxyethoxy)ethoxy]phenylacetamide 60 mg (0.224 mmol) of the compound obtained in Example 59-2 was dissolved in 15 ml of dichloromethane, and then 0.005 ml of N,N-dimethylfornamide and 0.05 ml (0.685 mmol) of thionyl chloride were added thereto. The mixture was stirred for one hour. The solvent and the unreacted thionyl chloride were removed under reduced pressure. The resultant was dissolved in 15 ml of tetrahydrofuran, and 79 mg (0.203 mmol) of the compound obtained in Preparation 1 was added thereto. The mixture was heated to reflux for 2 hours. After cooled to room temperature, 1 ml (2 mmol) of aqueous 2N sodium hydroxide solution was added and the mixture was stirred at room temperature for 10 hours. After the reaction was completed, the mixture was concentrated and 30 ml of water was added. The mixture was extracted with 20 ml of ethyl acetate and then concentrated again. 37 mg (0.074 mmol, yield 36%) of the title compound was isolated by silica gel column chromatography.

$^1$H NMR (CDCl$_3$, ppm): δ 1.20 (3H, t), 2.51 (2H, t), 3.32 (2H, q), 3.52 (2H, t), 3.62–3.87 (10H, m), 4.15 (2H, t), 6.90 (2H, d), 7.27 (2H, d), 7.50 (1H, d), 7.76(1H, d), 7,82 (1H, s), 9.80 (1H, s); FAB MS(m/e)=503 [M+1].

Example 60

Synthesis of 2-(2-Amino-1,3-thiazol-4-yl)-N-[5-(1,1-dioxo-1λ$^6$-isothiazolidin-2-yl)-1H-indazol-3-yl]acetamide(60)

0.1 g (0.203 mmol) of the compound obtained in Example 58 was dissolved in 15 ml of dichloromethane, and then 6 ml of trifluoroacetic acid was added thereto. The mixture was stirred at room temperature for two hours. The solvent was removed under reduced pressure to give 40 mg of the title compound in a yield of 50%.

$^1$H NMR (CD$_3$OD, ppm): δ 2.50 (2H, m), 3.42 (2H, t), 3.70 (2H, s), 3.80 (2H, t), 6.45 (1H, s), 7.46 (2H, m), 7.70 (1H, s); ESI MS(m/e)=393 [M+1].

Example 61

Synthesis of 2-[4-(4-Bromophenyl)-1H-imidazol-1-yl]-N-[5-(1,1-dioxo-1λ$^6$-isothiazolidin-2-yl)-1H-indazol-3-yl]acetamide(61)

10 mg of the title compound was obtained in a yield of 10% according to the same procedure as Example 41, except that 4-(4-bromophenyl)imidazole was used instead of benzimidazole.

$^1$H NMR (CD$_3$OD, ppm): δ 2.47 (2H, m), 3.39 (2H, t), 3.77 (2H, t), 5.05 (2H, s), 7.43 (2H, s), 7.46 (2H, d), 7.52 (1H, s), 7.60 (2H, d), 7.69 (1H, s), 7.75 (1H, s); ESI MS(m/e)=515 [M+1].

Example 62

Synthesis of N-[5-(1,1-Dioxo-1λ$^6$-isothiazolidin-2-yl)-1H-indazol-3-yl]-2-[4-(2-naphthyl)-1H-imidazol-1-yl]acetamide(62)

20 mg of the title compound was obtained in a yield of 21% according to the same procedure as Example 41, except that 4-(2-naphthyl)imidazole was used instead of benzimidazole.

$^1$H NMR (CDCl$_3$+CD$_3$OD, ppm): δ 2.42 (2H, m), 3.34 (2H, t), 3.72 (2H, t), 4.96 (2H, s), 7.38 (4H, m), 7.51 (1H, m), 7.77 (6H, m), 8.16 (1H, s); ESI MS(m/e)=487 [M+1].

Example 63

Synthesis of 2-(4-[1,1'-Biphenyl]-4-yl-1H-imidazol-1-yl)-N-[5-(1,1-dioxo-1λ$^6$-isothiazolidin-2-yl)-1H-indazol-3-yl]acetamide(63)

15 mg of the title compound was obtained in a yield of 10% according to the same procedure as Example 41, except that 4-([1,1'-biphenyl]-4-yl)imidazole was used instead of benzimidazole.

$^1$H NMR (CDCl$_3$+CD$_3$OD, ppm): δ 2.48 (2H, m), 3.36 (2H, t), 3.76 (2H, t), 4.95 (2H, s), 7.29 (1H, m), 7.39 (3H, m), 7.45 (1H, d), 7.59 (5H, m), 7.70 (2H, d), 7.77 (2H, d); ESI MS(m/e)=513 [M+1].

Example 64

Synthesis of N-[5-(1,1-Dioxo-1λ$^6$-isothiazolidin-2-yl)-1H-indazol-3-yl]-2-[2-(ethylamino)-1,3-thiazol-4-yl]acetamide(64)

Example 65

Synthesis of 2-[2-(Diethylamino)-1,3-thiazol-4-yl]-N-[5-(1,1-dioxo-1λ$^6$-isothiazolidin-2-yl)-1H-indazol-3-yl]acetamide(65)

36 mg (0.092 mmol) of the compound obtained in Example 60 was dissolved in 15 ml of N,N-dimethylformamide, and then 0.016 ml (3.0 eq) of acetaldehyde and 40 mg of sodium triacetoxyborohydride 40 mg were added thereto. The mixture was stirred for 12 hours. The solvent was removed under reduced pressure, and then the residue was purified by silica gel column chromatography (eluent:dichloromethane/methanol=19/1(v/v)) to give 2 mg of the compound of Example 64 in a yield of 5% and 3 mg of the compound of Example 65 in a yield of 7%.

Example 64

N-[5-(1,1-Dioxo-1λ$^6$-isothiazolidin-2-yl)-1H-indazol-3-yl]-2-[2-(ethylamino)-1,3-thiazol-4-yl] acetamide $^1$H NMR (CDCl$_3$+CD$_3$OD, ppm): δ 1.25 (3H, t), 2.52 (2H, m), 3.29 (2H, m), 3.40 (2H, t), 3.66 (2H, s), 3.81 (2H, t), 6.36 (1H, s), 7.42 (2H, m), 7.73 (1H, s); API MS(m/e)=421 [M+1].

Example 65

2-[2-(Diethylamino)-1,3-thiazol-4-yl]-N-[5-(1,1-dioxo-1λ$^6$-isothiazolidin-2-yl)-1H-indazol-3-yl] acetamide $^1$H NMR (CDCl$_3$+CD$_3$OD, ppm): δ 1.24 (6H, m), 2.53 (2H, m), 3.30 (2H, m), 3.40 (2H, t) 3.40 (2H, m), 3.81 (2H, t), 4.39 (2H, s), 6.38 (1H, d), 7.43 (2H, m), 7.71 (1H, d); ESI MS(m/e)=449 [M+1].

Example 66

Synthesis of N-[5-(1,1-Dioxo-1λ$^6$-isothiazolidin-2-yl)-1H-indazol-3-yl]-2-(4-2-[2-(2-methoxyethoxy) ethoxy]ethoxyphenyl)acetamide(66)

68 mg (0.128 mmol) of the title compound was obtained in a yield of 34% according to the same procedure as Example 59, except that 2-[2-(2-methoxyethoxy)ethoxy] ethanol was used instead of 2-(2-ethoxyethoxy)ethanol.

$^1$H NMR (DMSO-d$_6$, ppm): δ 2.51 (2H, t), 3.22 (3H, s), 3.32–3.81 (16H, m), 4.15 (2H, t), 6.91 (2H, d), 7.29 (2H, d), 7.40 (1H, d), 7.44 (1H, d), 7.53 (1H, s); 10.50 (1H, s), FAB MS(m/e)=533 [M+1].

Example 67

Synthesis of N-[5-(1,1-Dioxo-1λ$^6$-isothiazolidin-2-yl)-1H-indazol-3-yl]-2-(4-ethoxy-3-nitrophenyl) acetamide(67)

67-1) Synthesis of 4-Ethoxy-3-nitrophenylacetic Acid 1.08 g (6.0 mmol) of 4-ethoxyphenylacetic acid was dissolved in 12 ml of acetic anhydride, and then 1.45 g (6.0 mmol) of cupric nitrate was added thereto. The mixture was stirred at 0° C. for one hour. The resulting mixture was extracted with ethyl acetate, and then washed with water three times. The solvent was removed under reduced pressure, and then the residue was purified by silica gel column chromatography (eluent:dichloromethane/methanol=95/5(v/v)) to give 1.30 mg of the title compound in a yield of 94%.

$^1$H NMR (CDCl$_3$, ppm): δ 1.44 (3H, t), 3.62 (2H, s), 4.16 (2H, q), 7.02 (1H, d), 7.41 (1H, d) 7.73 (1H, s); ESI MS(m/e)=224 [M+1].

67-2) Synthesis of 4-Ethoxy-3-nitrophenylacetyl Chloride 153 mg (0.68 mmol) of the compound obtained in Example 67-1 was dissolved in dichloromethane, and then 0.15 ml (2.04 mmol) of thionyl chloride was added thereto. The mixture was stirred for 2 hours. The solvent was removed under reduced pressure to give the title compound quantatively.

67-3) Synthesis of N-[5-(1,1-Dioxo-1λ$^6$-isothiazolidin-2-yl)-1H-indazol-3-yl]-2-(4-ethoxy-3-nitrophenyl)acetamide 190 mg of the title compound was obtained in a yield of 79% according to the same procedure as Example 2, except that the compound obtained in Example 67-2 was used instead of 3-chlorophenylacetyl chloride.

$^1$H NMR (DMSO-d6, ppm): δ 1.34 (3H, t), 2.39 (2H, m), 2.04 (2H, t), 3.46 (2H, t), 3.68 (2H, t), 3.78 (2H, s), 4.21 (2H, q), 7.34 (1H, d), 7.35 (1H, d), 7.47 (1H, d), 7.56 (1H, s), 7.63 (1H, d), 7.87 (1H, s), 10.65 (1H, s); ESI MS(m/e)=460 [M+1].

Example 68

Synthesis of N-[5-(1,1-Dioxo-1λ$^6$-isothiazolidin-2-yl)-1H-indazol-3-yl]-2-(2-methylphenyl)acetamide (68)

32 mg of the title compound was obtained in a yield of 64% according to the same procedure as Example 2, except that (2-methylphenyl)acetyl chloride was used instead of 3-chlorophenylacetyl chloride.

$^1$H NMR (DMSO-d$_6$, ppm): δ 2.23 (3H, s), 2.39 (2H, m), 3.46 (2H, t), 3.68 (2H, t), 3.77 (2H, s), 7.17 (3H, m), 7.31 (2H, m), 7.34 (1H, d), 7.46 (1H, d), 7.58 (1H, s); ESI MS(m/e)=385 [M+1].

Example 69

Synthesis of N-[5-(1,1-Dioxo-1λ$^6$-isothiazolidin-2-yl)-1H-indazol-3-yl]-2-[3-(ethylamino)phenyl] acetamide(69)

30 mg (0.78 mmol) of the compound obtained in Example 21 was added to 5 ml of N,N-dimethylformamide, and 10 mg (0.234 mmol) of acetaldehyde, 50 mg (0.234 mmol) of sodium triacetoxyborohydride and 14 mg (0.234 mmol) of glacial acetic acid were added. The mixture was stirred for 15 hours. After the removal of the solvent under reduced pressure, ethyl acetate and water was added. After basified with aqueous 1N sodium hydroxide solution, ethyl acetate layer was collected and it was washed with water three times. The solvent was removed under reduced pressure, and the residue was then purified by silica gel column chromatography (eluent:ethyl acetate) to give 10 mg of the title compound in a yield of 31%.

$^1$H NMR (CDCl$_3$, ppm): δ 1.18 (3H, t), 2.39 (2H, m), 3.04 (2H, q), 3.61 (2H, t), 3.64 (2H, s), 6.47 (1H, d), 6.54 (1H, s), 6.63 (1H, d), 7.03 (1H, d), 7.10 (1H, t), 7.25 (1H, s), 7.60 (1H, s), 8.58 (1H, s); ESI MS(m/e)=414 [M+1].

Example 70

Synthesis of 2-[3-(Diethylamino)phenyl]-N-[5-(1,1-dioxo-1λ⁶-isothiazolidin-2-yl)-1H-indazol-3-yl]acetamide(70)

The compound extracted with ethyl acetate in Example 69 was purified by silica gel column chromatography (eluent:ethylacetate) to give 3 mg of the title compound in a yield of 9%.

¹H NMR (CDCl₃, ppm): δ 1.15 (6H, t), 2.48 (2H, m), 3.35 (6H, m), 3.74 (2H, s), 3.76 (2H, t), 6.62 (3H, m), 7.21 (2H, d), 7.42 (1H, d), 7.76 (1H, s), 8.07 (1H, s); ESI MS(m/e)=442 [M+1].

Example 71

Synthesis of 2-(3,5-Dimethoxyphenyl)-N-[5-(1,1-dioxo-1λ⁶-isothiazolidin-2-yl)-1H-indazol-3-yl]acetamide(71)

50 mg of the title compound was obtained in a yield of 89% according to the same procedure as Example 2, except that 3,5-dimethoxyphenylacetyl chloride was used instead of 3-chlorophenylacetyl chloride.

¹H NMR (DMSO-d₆, ppm): δ 2.40 (2H, m), 3.46 (2H, t), 3.64 (2H, s), 3.68 (2H, t), 3.74 (6H, s), 5.75 (1H, s), 6.40 (1H, s), 6.57 (1H, s), 7.35 (1H, d), 7.46 (1H, d), 7.55 (1H, s), 10.57 (1H, s); ESI MS(m/e)=431 [M+1].

Example 72

Synthesis of N-[5-(1,1-Dioxo-1λ⁶-isothiazolidin-2-yl)-1H-indazol-3-yl]-2-[4-(ethylamino)phenyl]acetamide(72)

15 mg (0.039 mmol) of the compound obtained in Example 21 was dissolved in 5 ml of N,N-dimethylformamide, and 5 mg (0.117 mmol) of acetaldehyde, 25 mg (0.117 mmol) of sodium triacetoxyborohydride and 7 mg (0.117 mmol) of glacial acetic acid were. After stirring for 15 hours, solvent was removed under reduced pressure, and ethyl acetate and water was added to the residue. After basified with aqueous 1N sodium hydroxide solution, ethyl acetate layer was collected and it was washed with water three times. The solvent was removed under reduced pressure, and the residue was then purified by silica gel column chromatography (eluent:ethylacetate) to give 5 mg of the title compound in a yield of 31%.

¹H NMR (DMSO-d₆, ppm): δ 1.14 (3H, t), 2.39 (2H, m), 3.01 (2H, m), 3.46 (2H, t), 3.52 (2H, s), 3.67 (2H, t), 5.39 (1H, s), 6.52 (2H, d), 7.09 (2H, d), 7.34 (1H, d), 7.45 (1H, d), 7.54 (1H, s), 10.44 (1H, s); ESI MS(m/e)=414 [M+1].

Example 73

Synthesis of 2-[4-(Diethylamino)phenyl]-N-[5-(1,1-dioxo-1λ⁶-isothiazolidin-2-yl)-1H-indazol-3-yl]acetamide(73)

The compound extracted with ethyl acetate in Example 73 was purified by silica gel column chromatography (eluent:ethylacetate) to give 1 mg of the title compound in a yield of 6%.

¹H NMR (CDCl₃+CD₃OD, ppm): δ 1.11 (6H, t), 2.58 (2H, m), 3.31 (4H, q), 3.35(2H, t), 3.65(2H, s), 3.79(2H, t), 6.65(2H, d), 7.16(2H, d), 7.32(1H, d), 7.44 (1H, s), 7.75(1H, s); ESI MS(m/e)=442 [M+1].

Example 74

Synthesis of 2-(3-Chloro-4-ethoxyphenyl)-N-[5-(1,1-dioxo-1λ⁶-isothiazolidin-2-yl)-1H-indazol-3-yl]acetamide(74)

47 mg of the title compound was obtained in a yield of 81% according to the same procedure as Example 2, except that 3-chloro-4-ethoxyphenylacetyl chloride was used instead of 3-chlorophenylacetyl chloride.

¹H NMR (DMSO-d₆, ppm): δ 1.35(3H, t), 2.40(2H, m), 3.46(2H, t), 3.67(2H, s), 3.68(2H, t), 4.10(2H, q), 7.11(1H, d), 7.35(1H, d), 7.43(1H, s), 7.46(2H, d), 7.55(1H, s), 10.59(1H, s); ESI MS(m/e)=449 [M+1].

Example 75

Synthesis of 2-[4-(2-Aminoethoxy)phenyl]-N-[5-(1,1-dioxo-1λ⁶-isothiazolidin-2-yl)-1H-indazol-3-yl]acetamide(75)

75-1) Synthesis of Benzyl 2-Hydroxyethylcarbamate 944 mg(15.46 mmol) of 2-aminoethanol was dissolved in 50 ml of dichloromethane, and then 1.8 ml(12.88 mmol) of benzyl chloroformate and 2.7 ml(19.32 mmol) of triethylamine were added thereto. After the reaction was completed, the mixture was concentrated and 50 ml of water was added to obtain a white solid. The obtained white solid was filtered and dried to give 1.94 g(9.93 mmol) of the title compound in a yield of 77%.

¹H NMR (CDCl₃, ppm): δ 3.34(2H, t), 3.71(2H, t), 5.10(2H, s), 7.35–7.39(5H, m); FAB MS(m/e)=196 [M+1].

75-2) Synthesis of methyl 2-[4-(2-[(benzyloxy)carbonyl]aminoethoxy)phenyl]acetate 950 mg(4.87 mmol) of the compound obtained in Example 75-1 and 809 mg(4.87 mmol) of 4-hydroxyphenylacetic acid methyl ester were dissolved in 70 ml of tetrahydrofuran, and then 0.84 ml(5.35 mmol) of diethylazodicarboxylate and 1.4 g(5.35 mmol) of triphenylphosphine were added thereto. The mixture was stirred at room temperature for one hour. After the reaction was completed, the solvent was removed under reduced pressure. Addition of 40 ml of diethyl ether to the residue caused precipitation. The mixture was stirred for 30 minutes and filtered. The filtrate was purified by silica gel column chromatography to give 1.28 g(3.73 mmol) of the title compound in a yield of 77%.

¹H NMR (CDCl₃, ppm): δ 3.54(3H, s), 3.59(2H, t), 3.67(2H, s), 4.01(2H, t), 5.10(2H, s), 6.82(2H, d), 7.17(2H, d), 7.35–7.39(5H, m); FAB MS(m/e)=344 [M+1].

75-3) Synthesis of 2-[4-(2-[(Benzyloxy)carbonyl]aminoethoxy)phenyl]acetic Acid 1.27 g(3.70 mmol) of the compound obtained in Example 75-2 was dissolved in a solution consisting of 30 ml of tetrahydrofuran, 10 ml of methanol and 10 ml of water, and then 233 mg(5.55 mmol) of lithium hydroxide was added thereto. The mixture was stirred at room temperature for 15 hours. After the reaction was completed, the mixture was concentrated and 70 ml of water was added thereto. The mixture was adjusted to pH of 3 with aqueous 1N hydrochloric acid solution to obtain a white solid. The solid thus obtained was filtered, washed with water and dried to give 730 mg(2.22 mmol) of the title compound in a yield of 60%.

¹H NMR (CD₃OD, ppm): δ 3.60(2H, t), 3.71(2H, s), 4.05(2H, t), 5.10(2H, s), 6.82(2H, d), 7.17(2H, d), 7.35–7.39 (5H, m); FAB MS(m/e)=330 [M+1].

75-4) Synthesis of Benzyl 3-(2-[4-(2-[(benzyloxy)carbonyl]aminoethoxy)phenyl]acetylamino)-5-(1,1-dioxo-1λ⁶-isothiazolidin-2-yl)-1H-indazol-1-carboxylate 127 mg(0.386 mmol) of the compound obtained in Example 75-3 was dissolved in 20 ml of dichloromethane, and then 0.001 ml of N,N-dimethylformamide and 0.05 ml(0.685mmol) of thionyl chloride were added thereto. The mixture was stirred at room temperature for one hour. After the reaction was completed, the mixture was concentrated and dissolved in 20 ml of tetrahydrofuran. 99 mg(0.257 mmol) of the compound obtained in Preparation 1 was added thereto, and the produced mixture was heated to reflux for 2 hours. After the reaction was completed, 30 ml of water was added and the mixture was extracted with 20 ml of ethyl acetate. After removal of the solvent, concentrated, the residue was purified by silica gel column chromatography to give 170 mg(0.243 mmol) of the title compound in a yield of 95%.

$^1$H NMR (CDCl$_3$, ppm): δ 2.53(2H, t), 3.39(2H, t), 3.60(2H, t), 3.71(2H, s), 3.83(2H, t), 4.05(2H, t) 5.11(2H, s), 5.47(2H, s), 6.85(2H, d), 7.20(2H m), 7.38–7.40(2H, m), 7.66(1H, d), 8.11(1H, s); FAB MS(m/e)=698 [M+1].

75-5) Synthesis of 2-[4-(2-Aminoethoxy)phenyl]-N-[5-(1,1-dioxo-1λ$^6$-isothiazolidin-2-yl)-1H-indazol-3-yl]acetamide 82 mg(0.118 mmol) of the compound obtained in Example 75-4 was dissolved in a solution of 20 ml methanol and 10 ml of dichloromethane, and catalytic amount of palladium-adsorbed activated carbon(10%) was added thereto. The mixture was stirred under hydrogen atmosphere for 2 hours. After the reaction was completed, the product was filtered through celite. The removal of solvent under reduced pressure gave 32 mg(0.075 mmol) of the title compound in a yield of 63%.

$^1$H NMR (CD$_3$OD, ppm): δ 2.50(2H, t), 3.30(2H, t), 3.34(2H, t), 3.43(2H, t), 3.78(2H, s), 4.05(2H, t), 6.95(2H, d), 7.34(2H, d), 7.40–7.52(2H, m), 7.66(1H, d); FAB MS(m/e)=430 [M+1].

Example 76

Synthesis of 2-[2-(Acetylamino)-1,3-thiazol4-yl]-N-[5-(1,1-dioxo-1λ$^6$-isothiazolidin-2-yl)-1H-indazol-3-yl]acetamide(76)

After 40 mg(0.102 mmol) of the compound obtained in Example 60 was dissolved in 5 ml of N,N-dimethylformamide, were added 0.01 ml(1.5 eq) of acetic acid, 33 mg(1.7 eq) of 1-(3-dimethylaminopropyl)-3-ethylcarbodiimide hydrochloric acid salt and 32 mg(2.3 eq) of hydroxybenzotriazole. The mixture was stirred for 12 hours. The solvent was removed under reduced pressure, and then the residue was purified by silica gel column chromatography (eluent:dichloromethane/methanol=93/7(v/v)) to give 5 mg of the title compound in a yield of 11%.

$^1$H NMR (CDCl$_3$+CD$_3$OD, ppm): δ 2.53(2H, m), 2.66 (3H, s), 3.42(2H, t), 3.67(2H, s), 3.83(2H, t), 6.35(1H, s), 7.52(1H, dd), 7.84(1H, s), 8.32(1H, d); ESI MS(m/e)=435 [M+1].

Example 77

Synthesis of 2-(2-14-(Benzyloxy)benzyllamino-1,3-thiazol-4-yl)-N-[5-(1,1-dioxo-1λ$^6$-isothiazolidin-2-yl)-1H-indazol-3-yl]acetamide(77)

77-1) Synthesis of 2-[2-([4-(Benzyloxy)phenyl] methylideneamino)-1,3-thiazol-4-yl]-N-[5-(1,1-dioxo-1λ$^6$-isothiazolidin-2-yl)-1H-indazol-3-yl]acetamide After 50 mg(0.128 mmol) of the compound obtained in Example 60 was dissolved in 8 ml of N,N-dimethylformamide, were added 81 mg(3.0 eq) of 4-benzyloxybenzaldehyde, 0.1 g(4 eq) of sodium triacetoxyborohydride and 0.4 ml(5 eq) of acetic acid. The mixture was stirred for 12 hours. The solvent was removed under reduced pressure, and then the residue was purified by silica gel column chromatography (eluent dichloromethane/methanol=93/7(v/v)) to give 20 mg of the title compound in a yield of 26%.

$^1$H NMR (CDCl$_3$+CD$_3$OD, ppm): δ 2.16(2H, m), 3.03 (2H, t), 3.49(2H, t), 3.64(2H, s), 4.87(2H, s), 6.79(1H, d), 6.91(1H, s), 7.11(6H, m), 7.40(1H, s), 7.64(1H, d), 8.59(1H, s); API MS(m/e)=587 [M+1].

77-2) Synthesis of 2-(2-[4-(Benzyloxy)benzyl]amino-1,3-thiazol-4-yl)-N-[5-(1,1-dioxo-1λ$^6$-isothiazolidin-2-yl)-1H-indazol-3-yl]acetamide 20 mg(0.034 mmol) of the compound obtained in Example 77-1 was dissolved in 20 ml of methanol, and then 60 mg of sodium borohydride was added thereto. After stirring 3.5 hours, the solvent was removed under reduced pressure. Filtration of the precipitate caused by removal of solvent gave the title compound quantatively.

$^1$H NMR (CDCl$_3$+CD$_3$OD, ppm): δ 2.45(2H, m), 3.35 (2H, t), 3.68(2H, s), 3.75(2H, t), 4.08(2H, m), 4.40(2H, s), 4.94(2H, s), 6.38(1H, s), 6.83(2H, d), 7.25(3H, m), 7.32(2H, m), 7.36(2H, m), 7.44(2H, m), 7.66(1H, s); API MS(m/e)= 589 [M+1].

Example 78

Synthesis of N-[5-(1,1-Dioxo-1λ$^6$-isothiazolidin-2-yl)-1H-indazol-3-yl]-2-(3-ethoxyphenyl)acetamide (78)

40 mg of the title compound was obtained in a yield of 48% according to the same procedure as Example 2, except that 3-ethoxyphenylacetyl chloride was used instead of 3-chlorophenylacetyl chloride.

$^1$H NMR (DMSO-d$_6$, ppm): δ 1.32(3H, t), 2.40(2H, m), 3.46(2H, t), 3.68(4H, m), 4.03(2H, q), 6.81(1H, d), 6.94(1H, d), 6.95(1H, s), 7.24(1H, t), 7.35(1H, d), 7.46(1H, d), 7.55(1H, s), 10.59(1H, s); ESI MS(m/e)=415 [M+1].

Example 79

Synthesis of N-[5-(1,1-Dioxo-1λ$^6$-isothiazolidin-2-yl)-1H-indazol-3-yl]-2-[4-ethoxy-3-(4-morpholinylsulfonyl)phenyl]acetamide(79)

79-1) Synthesis of ethyl 2-[3-(chlorosulfonyl)-4-ethoxyphenyl]acetate

After addition of 208 mg(1.0 mmol) of ethyl 2-(4-ethoxyphenyl)acetate to 0.2 ml(3.0 mmol) of chlorosulfuric acid dropwise at 0° C., the mixture was warmed to room temperature and stirred for one hour, and then poured into ice water. After the resultant was extracted with ethyl acetate, the extracted ethyl acetate solution was washed with water three times. The solvent was removed under reduced pressure to give 110 mg of the title compound in a yield of 34%.

$^1$H NMR (CDCl$_3$, ppm): δ 1.26(3H, t), 1.53(3H, t), 3.60(2H, s), 4.16(2H, q), 4.27(2H, q), 7.05(1H, d), 7.58(1H, d), 7.84(1H, s).

79-2) Synthesis of Ethyl 2-[4-Ethoxy-3-(4-morpholinylsulfonyl)phenyl]acetate 107 mg(0.35 mmol) of the compound obtained in Example 79-1 was dissolved in dichloromethane, and then 61 mg(0.7 mmol) of morpholine and 71 mg(0.7 mmol) of triethylamine were added thereto. The mixture was stirred for one hour. The solvent was removed under reduced pressure. After the resultant was extracted with ethyl acetate, the extracted ethyl acetate solution was washed with water three times. The solvent was removed under reduced pressure, and then the residue was purified by silica gel column chromatography (eluent: hexane/ethyl acetate=1/1 (v/v)) to give 106 mg of the title compound in a yield of 85%.

$^1$H NMR (CDCl$_3$, ppm): δ 1.24(3H, t), 1.46(3H, t), 3.24(4H, t), 3.57(2H, s), 3.71(4H, t), 4.14(4H, q), 6.95(1H, d), 7.42(1H, d), 7.77(1H, s); ESI MS(m/e)=358 [M+1].

79-3) Synthesis of Ethyl 2-[4-Ethoxy-3-(4-morpholinylsulfonyl)phenyl]acetic Acid 103 mg(0.288 mmol) of the compound obtained in Example 79-2 was dissolved in a solution of 3 ml of tetrahydrofuran/1 ml of methano/1 ml of water, and then 35 mg(0.864 mmol) of lithium hydroxide was added thereto. The mixture was stirred at room temperature for one hour. After the solvent was removed under reduced pressure, aqueous 1N HCl solution was added thereto to adjust to pH of 3. After the resulting mixture was extracted with ethyl acetate, the extracted ethyl acetate solution was washed with water three times. The solvent was removed under reduced pressure to give 94 mg of the title compound in a yield of 99%.

$^1$H NMR (CDCl$_3$, ppm): δ 1.45(3H, t), 3.24(4H, t), 3.61(2H, s), 3.70(4H, t), 4.14(2H, q), 6.96(1H, d), 7.42(1H, d), 7.76(1H, s); ESI MS(m/e)=330 [M+1].

79-4) Synthesis of Ethyl 2-[4-Ethoxy-3-(4-morpholinylsulfonyl)phenyl]acetyl Chloride 94 mg(0.28 mmol) of the compound obtained in Example 79-3 was dissolved in dichloromethane, and then 100 mg(0.84 mmol) of thionyl chloride was added thereto. The mixture was stirred at room temperature for 2 hours. The solvent was removed under reduced pressure to give the title compound quantitatively.

79-5) Synthesis of N-[5-(1,1-Dioxo-1λ$^6$-isothiazolidin-2-yl)-1H-indazol-3-yl]-2-[4-ethoxy-3-(4-morpholinylsulfonyl)phenyl]acetamide 80 mg of the title compound was obtained in a yield of 70% according to the same procedure as Example 2, except that the compound obtained in Example 97-4 was used instead of 3-chlorophenylacetyl chloride.

$^1$H NMR (DMSO-d$_6$, ppm): δ 1.36(3H, t), 2.39(2H, m), 3.09(4H, t), 3.46(2H, t), 3.59(4H, t), 3.68(2H, t), 3.74(2H, s), 4.16(2H, q), 7.24(1H, d), 7.35(1H, d), 7.46(1H, d), 7.54(1H, s), 7.62(1H, d), 7.79(1H, s), 10.66(1H, s); ESI MS(m/e)=564 [M+1].

Example 80

Synthesis of 2-[3-(Aminosulfonyl)4-ethoxyphenyl]-N-[5-(1,1-dioxo-1λ$^6$-isothiazolidin-2-yl)-1H-indazol-3-yl]acetamide(80)

80-1) Synthesis of 5-(2-[5-(1,1-Dioxo-1λ$^6$-isothiazolidin-2-yl)-1H-indazol-3-yl]amino-2-oxoethyl)-2-ethoxybenzenesulfonyl chloride 20 mg(0.048 mmol) of the compound obtained in Example 42 was added to 0.2 ml of chlorosulfuric acid dropwise at 0° C. After stirring for 10 minutes, the mixture was poured into ice water. The resultant was extracted with ethyl acetate, and then the extracted ethyl acetate solution was washed with water three times. The solvent was removed by evaporation under reduced pressure, and then the residue was purified by silica gel column chromatography (eluent: ethyl acetate) to give 3 mg of the title compound in a yield of 12%.

$^1$H NMR (DMSO-d$_6$, ppm): δ 1.30(3H, t), 2.39(2H, m), 3.45(2H, t), 3.68(2H, t), 3.72(2H, s), 4.02(2H, q), 6.93(2H, d), 7.28(1H, d), 7.35(1H, d), 7.45(1H, s), 7.76(1H, s), 10.61(1H, s);

80-2) Synthesis of 2-[3-(Aminosulfonyl)-4-ethoxyphenyl]-N-[5-(1,1-dioxo-1λ$^6$-isothiazolidin-2-yl)-1H-indazol-3-yl] acetamide 10 mg(0.019 mmol) of the compound obtained in Example 80-1 was dissolved in 5 ml of acetonitrile, and then 0.1 ml of ammonia water was added thereto. The mixture was stirred for 2 hours. The resultant was extracted with ethyl acetate, and then the extracted ethyl acetate solution was washed with water three times. After the solvent was removed by evaporation under reduced pressure, the residue was treated with diethyl ether to give 5 mg of the title compound as a solid in a yield of 56%.

$^1$H NMR (DMSO-d$_6$, ppm): δ 1.37(3H, t), 2.39(2H, m), 3.45(2H, t), 3.68(2H, t), 3.72(2H, s), 4.20(2H, q), 6.90(2H, s), 7.19(1H, d), 7.35(1H, d), 7.46(1H, d), 7.54(1H, d), 7.55(1H, s), 7.80(1H, s), 10.67(1H, s); ESI MS(m/e)=494 [M+1].

Example 81

Synthesis of N-[5-(1,1-Dioxo-1λ$^6$-isothiazolidin-2-yl)-1H-indazol-3-yl]-2-4-ethoxy-3-[(4-methyl-1-piperazinyl)sulfonyl]phenylacetamide(81)

7 mg(0.014 mmol) of the compound obtained in Example 80-1 was dissolved in 5 ml of dichloromethane, and then 0.1 ml of N-methylpiperazine was added thereto. The mixture was stirred for 15 hours. The resultant was extracted with ethyl acetate, and then the extracted ethyl acetate solution was washed with water three times. After the solvent was removed by evaporation under reduced pressure, the residue was purified by silica gel column chromatography (eluent: dichloromethane/methanol=9:1) to give 2 mg of the title compound in a yield of 25%.

$^1$H NMR (CDCl$_3$, ppm): δ 1.42(3H, t), 2.28(3H, s), 2.44(4H, br), 2.49(2H, m), 3.28(4H, br), 3.39(2H, t), 3.72(2H, s), 3.74(2H, t), 4.05(2H, q), 6.90(1H, d), 7.19(1H, d), 7.38(1H, d), 7.47(1H, d), 7.57(1H, s), 7.89(1H, s), 8.66(1H, s); ESI MS(m/e)=577 [M+1].

Example 82

Synthesis of 2-14-(2-Aminoethoxy)phenyl-N-[5-(1,1-dioxo-1λ$^6$-isothiazolidin-2-yl)-1H-indazol-3-yl] acetamide (82)

82-1) Synthesis of Benzyl 2-hydroxyethylcarbamate 944 mg(15.46 mmol) of 2-aminoethanol was dissolved in 50 ml of dichloromethane, and then 1.8 ml(12.88 mmol) of benzyl chloroformate and 2.7 ml(19.32 mmol) of triethylamine were added thereto. The mixture was stirred at room temperature for one hour. After the reaction was completed, the mixture was concentrated and 50 ml of water was added thereto to obtain a white solid. The obtained white solid was filtered and dried to give 1.94 g(9.93 mmol) of the title compound in a yield of 77%.

$^1$H NMR (CDCl$_3$, ppm): δ 3.34(2H, t), 3.71(2H, t), 5.10(2H, s), 7.35–7.39(5H, m); FAB MS(m/e)=196 [M+1].

82-2) Synthesis of Methyl 2-[4-(2-[(benzyloxy)carbonyl]aminoethoxy)phenyl]acetate 950 mg(4.87 mmol) of the compound obtained in Example 82-1 and 809 mg(4.87 mmol) of 4-hydroxyphenylacetic acid methyl ester were dissolved in 70 ml of tetrahydrofuran, and then 0.84 ml(5.35 mmol) of diethylazodicarboxylate and 1.4 g(5.35 mmol) of triphenylphosphine were added thereto. The mixture was stirred at room temperature for one hour. After the reaction was completed, the mixture was concentrated and 40 ml of diethyl ether was added thereto. The mixture was stirred for 30 minutes and the obtained precipitate was filtered. The filtrate was purified by silica gel column chromatography to give 1.28 g(3.73 mmol) of the title compound in a yield of 77%.

$^1$H NMR (CDCl$_3$, ppm): δ 3.54(3H, s), 3.59(2H, t), 3.67(2H, s), 4.01(2H, t), 5.10(2H, s), 6.82(2H, d), 7.17(2H, d), 7.35–7.39(5H, m); FAB MS(m/e)=344 [M+1].

82-3) Synthesis of 2-[4-(2-[(Benzyloxy)carbonyl]aminoethoxy)phenyl]acetic Acid 1.27 g(3.70 mmol) of the compound obtained in Example 82-2 was dissolved in a solution consisting of 30 ml of tetrahydrofuran, 10 ml of methanol and 10 ml of water, and then 233 mg(5.55 mmol) of lithium hydroxide was added thereto. The mixture was stirred at room temperature for 15 hours. After the reaction was completed, the mixture was concentrated and 70 ml of water was added thereto. The mixture was adjusted to pH of 3 with aqueous 1N hydrochloric acid solution to obtain a white solid. The solid thus obtained was filtered, washed with water and dried to give 730 mg(2.22 mmol) of the title compound in a yield of 60%.

$^1$H NMR (CD$_3$OD, ppm): δ 3.60(2H, t), 3.71(2H, s), 4.05(2H, t), 5.10(2H, s), 6.82(2H, d), 7.17(2H, d), 7.35–7.39 (5H, m); FAB MS(m/e)=330 [M+1].

82-4) Synthesis of Benzyl 3-(2-[4-(2-[(benzyloxy)carbonyl]aminoethoxy)phenyl]acetylamino)-5-(1,1-dioxo-1λ$^6$-isothiazolidin-2-yl)-1H-indazol-1-carboxylate 127 mg(0.386 mmol) of the compound obtained in Example 82-3 was dissolved in 20 ml of dichloromethane, and then 0.001 ml of N,N-dimethylformamide and 0.05 ml(0.685 mmol) of thionyl chloride were added thereto. The mixture was stirred at room temperature for one hour. After the reaction was completed, the mixture was concentrated and the residue was dissolved in 20 ml of tetrahydrofuran. 99 mg(0.257 mmol) of the compound obtained in Preparation 1 was added thereto, and the produced mixture was heated to reflux for 2 hours. After the solvent was removed under reduced pressure, 30 ml of water was added thereto and then the mixture was extracted with ethyl acetate. After the solvent was removed under reduced pressure, the residue was purified by silica gel column chromatography to give 170 mg(0.243 mmol) of the title compound in a yield of 95%.

$^1$H NMR (CDCl$_3$, ppm): δ 2.53(2H, t), 3.39(2H, t), 3.60(2H, t), 3.71(2H, s), 3.83(2H, t), 4.05(2H, t), 5.11(2H, s), 5.47(2H, s), 6.85(2H, d), 7.20(2H, d), 7.31–7.40(10H, m), 7.38–7.40(2H, m), 7.66(1H, d), 8.1 1(1H, s); FAB MS(m/e)=698 [M+1].

82-5) Synthesis of 2-[4-(2-Aminoethoxy)phenyl]-N-[5-(1,1-dioxo-1λ$^6$-isothiazolidin-2-yl)-1H-indazol-3-yl]acetamide 82 mg(0.118 mmol) of the compound obtained in Example 82-4 was dissolved in a solution of 20 ml methanol and 10 ml of dichloromethan, and catalytic amount of palladium-adsorbed activated carbon(10%) was added thereto. The mixture was stirred under hydrogen atmosphere for 2 hours. After the reaction was completed, the mixture was filtered through celtite. Removal of solvent under reduced pressure gave 32 mg(0.075 mmol) of the title compound in a yield of 63%.

$^1$H NMR (CD$_3$OD, ppm): δ 2.50(2H, t), 3.30(2H, t), 3.34(2H, t), 3.43(2H, t), 3.78(2H, s), 4.05(2H, t), 6.95(2H, d), 7.34(2H, d), 7.40–7.52(2H, m), 7.66(1H, d); FAB MS(m/e)=430 [M+1].

EXPERIMENTAL EXAMPLE

CDK2 and CDK4 Inhibitory Activity

Analytical experiments on inhibitory effects for CDK 2 and CDK 4 proteins were performed in accordance with Kitagawa's method(Kitagawa, M. et al.; Oncogene, 9: 2549, 1994) and Carlson's method(Carlson, B. A. et al.; Cancer Research 56: 2473, 1996), respectively. CDK2 enzyme was obtained from either extract from the worm cell co-infected with baculovirus which expresses a CDK2 gene and baculovirus which expresses a cyclin A gene, or active enzyme purified therefrom. CDK4 was also obtained from either extract from the worm cell co-infected with baculovirus which expresses a CDK4 gene and baculovirus which expresses a cyclin D1 gene. As substrates, histon H1 or Rb protein was used for CDK2, and Rb protein for CDK4. The radioactive activities in substrates were determined by reacting compounds diluted with each concentration with a proper quantity of CDK2/cyclin A or CDK4/cyclin D1 and substrate protein, and [gamma-32P labeled] ATP, and then separating the substrates.

Inhibitory abilities of inhibitors according to the present invention for each enzyme activity were expressed as IC50 values, which were determined in accordance with the method as described above. The results are shown in Table 1 below.

TABLE 1

| Comp. No. | CDK2 IC$_{50}$ (μM) | CDK2 IC$_{50}$ (μM) |
|---|---|---|
| 1 | <0.05 | <10 |
| 2 | <0.05 | <10 |
| 3 | <0.1 | <10 |
| 4 | <0.05 | <10 |
| 5 | <0.5 | >10 |
| 6 | <0.05 | <10 |
| 7 | <0.05 | <10 |
| 8 | <0.05 | <10 |
| 9 | <0.05 | <10 |
| 10 | <0.05 | <10 |
| 11 | <0.05 | <10 |
| 12 | <0.05 | <10 |
| 13 | <10 | <100 |
| 14 | <10 | <100 |
| 15 | <0.05 | <10 |
| 16 | <0.05 | <10 |
| 17 | <0.05 | <10 |
| 18 | <0.05 | <10 |
| 19 | >100 | >100 |
| 20 | <0.05 | <10 |
| 21 | <0.05 | <10 |
| 22 | <50 | <50 |
| 23 | <100 | >100 |
| 24 | <0.05 | <10 |
| 25 | <1 | <10 |
| 26 | <0.05 | <10 |
| 27 | <0.05 | <10 |
| 28 | <0.05 | <10 |
| 29 | <0.05 | <10 |
| 30 | <10 | <10 |
| 31 | <10 | <10 |
| 32 | <10 | <10 |
| 33 | <0.05 | <10 |
| 34 | <0.05 | <10 |
| 35 | <0.1 | <10 |
| 36 | <0.05 | <10 |
| 37 | <0.1 | <10 |
| 38 | <0.1 | <10 |
| 39 | <0.05 | <10 |
| 40 | <1.0 | <100 |
| 41 | <0.05 | <100 |
| 42 | <0.05 | <10 |
| 43 | <0.1 | <10 |
| 44 | <0.1 | <10 |
| 45 | <0.05 | <10 |
| 46 | <1.0 | <100 |
| 47 | <0.05 | <10 |
| 48 | <0.5 | <10 |
| 49 | <1.0 | <100 |
| 50 | <10 | <100 |
| 51 | <10 | <100 |
| 52 | <10 | <100 |
| 53 | <10 | <100 |
| 54 | <0.1 | <10 |
| 55 | <100 | <1000 |
| 56 | <100 | <1000 |
| 57 | <100 | <1000 |

TABLE 1-continued

| Comp. No. | CDK2 IC$_{50}$ ($\mu$M) | CDK2 IC$_{50}$ ($\mu$M) |
|---|---|---|
| 58 | <0.1 | <10 |
| 59 | <0.1 | <10 |
| 60 | <0.5 | <100 |
| 61 | <0.1 | <10 |
| 62 | <0.05 | <10 |
| 63 | <0.5 | <100 |
| 64 | <0.5 | <100 |
| 65 | <0.5 | <100 |
| 66 | <0.1 | <10 |
| 67 | <0.05 | <10 |
| 68 | <0.1 | <10 |
| 69 | <0.5 | <50 |
| 70 | <0.5 | <50 |
| 71 | <0.05 | <10 |
| 72 | <0.05 | <10 |
| 73 | <0.05 | <10 |
| 74 | <0.1 | <50 |
| 75 | <0.1 | <50 |
| 76 | <10 | <100 |
| 77 | <10 | <100 |
| 78 | <0.05 | <10 |
| 79 | <1.0 | <100 |
| 80 | <1.0 | <100 |
| 81 | <1.0 | <100 |
| 82 | <1.0 | <100 |

What is claimed is:

1. A compound represented by the following formula (1):

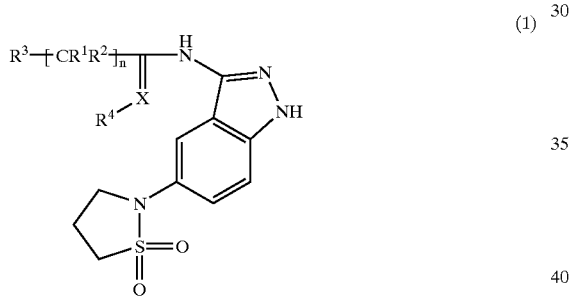

(1)

in which n represents 0, 1, 2 or 3,

X represents oxygen, sulfur or nitrogen atom, $R^1$ and $R^2$ each independently represent hydrogen, amino, hydroxy, lower alkyl or cycloalkyl, or together form cycloalkyl, $R^3$ represents hydrogen; lower alkyl; phenyl or naphthyl which may be unsubstituted or substituted with one to three substituents selected from the group consisting of hydroxy, halogen, nitro, amide, ester, carboxy, cyano, amidinyl, —O—$R^5$, —N$R^6R^7$, phenyl, alkylsulfanyl, $R^8$—SO$_2$—, lower alkyl, lower alkyl substituted with $R^9$, pyridinyl, piperidinyl, morpholinyl, piperazinyl, thienyl and furyl; aromatic and bicyclic aromatic compounds bearing at least one heteroatom selected from nitrogen, oxygen or sulfur atom; C$_{3-7}$-cycloalkyl bearing at least one heteroatom selected from nitrogen, oxygen or sulfur atom; piperazinyl, imidazolyl, morpholinyl or piperidinyl which may be unsubstituted or substituted with one or two substituents selected from the group consisting of lower alkyl, phenyl, phenyl substituted with halogen, phenyl substituted with alkoxy, phenyl substituted with alkylcarbonyl, biphenyl and naphthyl; thiazole which may be unsubstituted or substituted with amino, mono- or di- lower alkylamino, alkylcarbonylamino, benzylamino, benzyloxycarbonylamino, benzyloxybenzylamino or alkoxycarbonylamino; benzodioxol; isoquinoline; indolyl; or benzimidazole wherein $R^5$ represents phenyl, benzyl, lower alkyl, alkoxyalkyl, alkoxyalkoxylalkyl, alkoxyalkoxyalkoxyalkyl, aminoalkyl or mono- or di-alkylaminoalkyl, $R^6$ and $R^7$ are identical or different from each other and represent hydrogen, lower alkyl, oxygen or benzyl, or joined to form a ring, and $R^8$ and $R^9$ represent each independently lower alkyl, amino, morpholinyl, piperazinyl, N-alkylpiperazinyl or imidazole, and $R^4$ represents nothing when X is oxygen or sulfur atom, but represents hydroxy or alkoxy when X is nitrogen atom, pharmaceutically acceptable salt, solvated product or isomer thereof.

2. The compound of formula (1), or pharmaceutically acceptable salt, solvated product or isomer thereof according to claim 1, wherein n represents 1 or 2, X represents oxygen, sulfur or nitrogen atom, $R^1$ and $R^2$ each independently represent hydrogen, amino, hydroxy, lower alkyl or cycloalkyl, or together form cycloalkyl, $R^3$ represents hydrogen; lower alkyl; phenyl which may be unsubstituted or substituted with one to three substituents selected from the group consisting of hydroxy, halogen, nitro, amide, cyano, amidinyl, —O—$R^5$, —N$R^6R^7$, phenyl, lower alkylsulfanyl, $R^8$-SO$_2$—, lower alkyl, lower alkyl substituted with $R^9$, pyridinyl, piperidinyl, morpholinyl, thienyl and furyl; naphthyl; piperazinyl or imidazolyl which may be unsubstituted or substituted with one or two substituents selected from the group consisting of lower alkyl, phenyl, phenyl substituted with halogen, phenyl substituted with lower alkoxy, phenyl substituted with acetyl, biphenyl and naphthyl; morpholinyl; piperidinyl; thiazole which may be unsubstituted or substituted with amino, mono- or di- lower alkylamino, acetylamino, benzylamino, benzyloxyamino, benzyloxybenzylamino or lower alkoxycarbonylamino; benzodioxol; 3,4-dihydroisoquinoline; or benzimidazole wherein $R^5$ represents phenyl, benzyl, lower alkyl, lower alkoxyalkyl, polyethyleneglycolyl, aminoalkyl or mono- or di- lower alkylaminoalkyl, $R^6$ and $R^7$ are identical or different from each other and represent hydrogen, lower alkyl, oxygen or benzyl, or joined to form a ring, and $R^8$ and $R^9$ each independently represent lower alkyl, amino, morpholinyl, piperazinyl, N-alkylpiperazinyl or imidazole, and $R^4$ represents nothing when X is oxygen or sulfur atom, but represents hydroxy or alkoxy when X is nitrogen atom.

3. The compound of formula (1), or pharmaceutically acceptable salt, solvated product or isomer thereof according to claim 1, wherein the compound is selected from the group consisting of 1. N-[5-(1,1-dioxo-1$\lambda^6$-isothiazolidin-2-yl)-1H-indazol-3-yl]-2-phenylacetamide, 2. 2-(3-chlorophenyl)-N-[5-(1,1-dioxo-1$\lambda^6$-isothiazolidin-2-yl)-1H-indazol-3-yl]acetamide, 3. 2-[4-(benzyloxy)phenyl]-N-[5-(1,1-dioxo-1$\lambda^6$-isothiazolidin-2-yl)-1H-indazol-3-yl]acetamide, 4. N-[5-(1,1-dioxo-1$\lambda^6$-isothiazolidin-2-yl)-1H-indazol-3-yl]-2-(4-hydroxyphenyl)acetamide, 5. 2-[4-(dibenzylamino)phenyl]-N-[5-(1,1-dioxo-1$\lambda^6$-isothiazolidin-2-yl)-1H-indazol-3-yl]acetamide,
6. N-[5-(1,1-dioxo-1$\lambda^6$-isothiazolidin-2-yl)-1H-indazol-3-yl]-2-[4-(methylamino)phenyl]acetamide,
7. 2-(4-aminophenyl)-N-[5-(1,1-dioxo-1$\lambda^6$-isothiazolidin-2-yl)-1H-indazol-3-yl]acetamide,
8. 2-(4-chlorophenyl)-N-[5-(1,1-dioxo-1$\lambda^6$-isothiazolidin-2-yl)-1H-indazol-3-yl]acetamide,
9. N-[5-(1,1-dioxo-1$\lambda^6$-isothiazolidin-2-yl)-1H-indazol-3-yl]-2-(4-fluorophenyl)acetamide,
10. 2-[1,1'-biphenyl]-4-yl-N-[5-(1,1-dioxo-1$\lambda^6$-isothiazolidin-2-yl)-1H-indazol-3-yl]acetamide,
11. 2-(3-bromophenyl)-N-[5-(1,1-dioxo-1$\lambda^6$-isothiazolidin-2-yl)-1H-indazol-3-yl]acetamide,
12. 2-(4-bromophenyl)-N-[5-(1,1-dioxo-1$\lambda^6$-isothiazolidin-2-yl)-1H-indazol-3-yl]acetamide,
13. N-[5-(1,1-dioxo-1$\lambda^6$-isothiazolidin-2-yl)-1H-indazol-3-yl]-2-phenylethanethioamide,
14. N-[5-(1,1-dioxo-1$\lambda^6$-isothiazolidin-2-yl)-1H-indazol-3-yl]-N'-hydroxy-2-phenylethaneimidoamide,
15. 2-(1,3-benzodioxol-5-yl)-N-[5-(1,1-dioxo-1$\lambda^6$-isothiazolidin-2-yl)-1H-indazol-3-yl]acetamide,
16. N-[5-(1,1-dioxo-1$\lambda^6$-isothiazolidin-2-yl)-1H-indazol-3-yl]-2-(1-naphthyl)acetamide,
17. N-[5-(1,1-dioxo-1$\lambda^6$-isothiazolidin-2-yl)-1H-indazol-3-yl]-2-(2-naphthyl)acetamide,
18. N-[5-(1,1-dioxo-1$\lambda^6$-isothiazolidin-2-yl)-1H-indazol-3-yl]-2-(3-nitrophenyl)acetamide,
19. N-[5-(1,1-dioxo-1$\lambda^6$-isothiazolidin-2-yl)-1H-indazol-3-yl]acetamide,
20. N-[5-(1,1-dioxo-1$\lambda^6$-isothiazolidin-2-yl)-1H-indazol-3-yl]-2-[4-(methylsulfanil)phenyl]acetamide,
21. 2-(3-aminophenyl)-N-[5-(1,1-dioxo-1$\lambda^6$-isothiazolidin-2-yl)-1H-indazol-3-yl]acetamide,
22. N-[5-(1,1-dioxo-1$\lambda^6$-isothiazolidin-2-yl)-1H-indazol-3-yl]ethanethioamide,
23. N-[5-(1,1-dioxo-1$\lambda^6$-isothiazolidin-2-yl)-1H-indazol-3-yl]-N'-hydroxyethaneimidoamide,
24. 2-(3,4-dichlorophenyl)-N-[5-(1,1-dioxo-1$\lambda^6$-isothiazolidin-2-yl)-1H-indazol-3-yl]acetamide,
25. N-[5-(1,1-dioxo-1$\lambda^6$-isothiazolidin-2-yl)-1H-indazol-3-yl]-3-phenylpropanamide,
26. N-[5-(1,1-dioxo-1$\lambda^6$-isothiazolidin-2-yl)-1H-indazol-3-yl]-2-(4-isopropylphenyl)acetamide,
27. N-[5-(1,1-dioxo-1$\lambda^6$-isothiazolidin-2-yl)-1H-indazol-3-yl]-2-(3-methylphenyl)acetamide,
28. N-[5-(1,1-dioxo-1$\lambda^6$-isothiazolidin-2-yl)-1H-indazol-3-yl]-2-(4-methylphenyl)acetamide,
29. N-[5-(1,1-dioxo-1$\lambda^6$-isothiazolidin-2-yl)-1H-indazol-3-yl]-2-[4-(methylsulfonyl)phenyl]acetamide,
30. N-[5-(1,1-dioxo-1$\lambda^6$-isothiazolidin-2-yl)-1H-indazol-3-yl]-2-(4-methyl-1-piperazinyl)acetamide,
31. N-[5-(1,1-dioxo-1$\lambda^6$-isothiazolidin-2-yl)-1H-indazol-3-yl]-2-(4-morpholinyl)acetamide,
32. N-[5-(1,1-dioxo-1$\lambda^6$-isothiazolidin-2-yl)-1H-indazol-3-yl]-2-(1-piperidinyl)acetamide,
33. N-[5-(1,1-dioxo-1$\lambda^6$-isothiazolidin-2-yl)-1H-indazol-3-yl]-2-[4-(4-pyridinyl)phenyl]acetamide,
34. N-[5-(1,1-dioxo-1$\lambda^6$-isothiazolidin-2-yl)-1H-indazol-3-yl]-2-[4-(1-piperidinyl)phenyl]acetamide,
35. N-[5-(1,1-dioxo-1$\lambda^6$-isothiazolidin-2-yl)-1H-indazol-3-yl]-2-[4-(1-morpholinyl)phenyl]acetamide,
36. N-[5-(1,1-dioxo-1$\lambda^6$-isothiazolidin-2-yl)-1H-indazol-3-yl]-2-[4-(3-thienyl)phenyl]acetamide,
37. N-[5-(1,1-dioxo-1$\lambda^6$-isothiazolidin-2-yl)-1H-indazol-3-yl]-2-[4-(4-morpholinylsulfonyl)phenyl]acetamide,
38. N-[5-(1,1-dioxo-1$\lambda^6$-isothiazolidin-2-yl)-1H-indazol-3-yl]-2-(4-methoxyphenyl)acetamide,
39. N-[5-(1,1-dioxo-1$\lambda^6$-isothiazolidin-2-yl)-1H-indazol-3-yl]-2-[4-(2-furyl)phenyl]acetamide,
40. N-[5-(1,1-dioxo-1$\lambda^6$-isothiazolidin-2-yl)-1H-indazol-3-yl]-2-4-[(4-methyl-1-piperazinyl)sulfonyl]phenylacetamide,
41. 2-(1H-benzimidazol-1-yl)-N-[5-(1,1-dioxo-1$\lambda^6$-isothiazolidin-2-yl)-1H-indazol-3-yl]acetamide,
42. N-[5-(1,1-dioxo-1$\lambda^6$-isothiazolidin-2-yl)-1H-indazol-3-yl]-2-(4-ethoxyphenyl)acetamide,
43. N-[5-(1,1-dioxo-1$\lambda^6$-isothiazolidin-2-yl)-1H-indazol-3-yl]-2-[4-(4-morpholinylmethyl)phenyl]acetamide,
44. N-[5-(1,1-dioxo-1$\lambda^6$-isothiazolidin-2-yl)-1H-indazol-3-yl]-2-4-[(4-methyl-1piperazinyl)methyl]phenylacetamide,
45. N-[5-(1,1-dioxo-1$\lambda^6$-isothiazolidin-2-yl)-1H-indazol-3-yl]-2-(4-nitrophenyl)acetamide,
46. N-[5-(1,1-dioxo-1$\lambda^6$-isothiazolidin-2-yl)-1H-indazol-3-yl]-2-[4-(1H-imidazol-1-ylmethyl)phenyl]acetamide,
47. N-[5-(1,1-dioxo-1$\lambda^6$-isothiazolidin-2-yl)-1H-indazol-3-yl]-2-(4-phenyl-1H-imidazol-1-yl)acetamide,
48. N-[5-(1,1-dioxo-1$\lambda^6$-isothiazolidin-2-yl)-1H-indazol-3-yl]-2-(4-phenyl-1-piperazinyl) acetamide,
49. 2-[3,4-dihydro-2(1H)-isoquinolinyl]-N-[5-(1,1-dioxo-1$\lambda^6$-isothiazolidin-2-yl)-1H-indazol-3-yl]acetamide,
50. N-[5-(1,1-dioxo-1$\lambda^6$-isothiazolidin-2-yl)-1H-indazol-3-yl]-2-[4-(4-chlorophenyl)-1-piperazinyl]acetamide,
51. N-[5-(1,1-dioxo-1$\lambda^6$-isothiazolidin-2-yl)-1H-indazol-3-yl]-2-[4-(4-methoxyphenyl)-1-piperazinyl]acetamide,
52. N-[5-(1,1-dioxo-1$\lambda^6$-isothiazolidin-2-yl)-1H-indazol-3-yl]-2-[4-(2-etboxyphenyl)-1-piperazinyl]acetamide,
53. 2-[4-(4-acetylphenyl)-1-piperazinyl]-N-[5-(1,1-dioxo-1$\lambda^6$-isothiazolidin-2-yl)-1H-indazol-3-yl]acetamide,
54. N-[5-(1,1-dioxo-1$\lambda^6$-isothiazolidin-2-yl)-1H-indazol-3-yl]-2-(4-phenoxyphenyl)acetamide,
55. N-[5-(1,1-dioxo-1$\lambda^6$-isothiazolidin-2-yl)-1H-indazol-3-yl]-1-phenylcyclopentanecarboxamide,
56. 2-cyclopentyl-N-[5-(1,1-dioxo-1$\lambda^6$-isothiazolidin-2-yl)-1H-indazol-3-yl]-2-phenylacetamide,
57. N-[5-(1,1-dioxo-1$\lambda^6$-isothiazolidin-2-yl)-1H-indazol-3-yl]-2-phenylbutanamide,
58. t-butyl 4-(2-[5-(1,1-dioxo-1$\lambda^6$-isothiazolidin-2-yl)-1H-indazol-3-yl]amino-2-oxoethyl)-1,3-thiazol-2-ylcarbamate,
59. N-[5-(1,1-dioxo-1$\lambda^6$-isothiazolidin-2-yl)-1H-indazol-3-yl]-2-2-4-[2-(2-ethoxyethoxy)ethoxy]phenylacetamide,
60. 2-(2-amino-1,3-thiazol-4-yl)-N-[5-(1,1-dioxo-1$\lambda^6$-isothiazolidin-2-yl)-1H-indazol-3-yl]acetamide,
61. 2-[4-(4-bromophenyl)-1H-imidazol-1-yl]-N-[5-(1,1-dioxo-1$\lambda^6$-isothiazolidin-2-yl)-1H-indazol-3-yl]acetamide,
62. N-[5-(1,1-dioxo-1$\lambda^6$-isothiazolidin-2-yl)-1H-indazol-3-yl]-2-[4-(2-naphthyl)-1H-imidazol-1-yl]acetamide, 63. 2-(4-[1,1'-biphenyl]-4-yl-1H-imidazol-1-yl)-N-[5-(1,1-dioxo-1λ⁶-isothiazolidin-2-yl)-1H-indazol-3-yl]acetamide, 64. N-[5-(1,1-dioxo-1λ⁶-isothiazolidin-2-yl)-1H-indazol-3-yl]-2-[2-(ethylamimo)-1,3-thiazol-4-yl]acetamide, 65. 2-[2-(diethylamino)-1,3-thiazol-4-yl]-N-[5-(1,1-dioxo-1λ⁶-isothiazolidin-2-yl)-1H-indazol-3-yl]acetamide, 66. N-[5-(1,1-dioxo-1λ⁶-isothiazolidin-2-yl)-1H-indazol-3-yl]-2-(4-2-[2-methoxyethoxy)ethoxy]ethoxyphenyl)acetamide, 67. N-[5-(1,1-dioxo-1λ⁶-isothiazolidin-2-yl)-1H-indazol-3-yl]-2-(4-ethoxy-3-nitrophenyl)acetamide, 68. N-[5-(1,1-dioxo-1λ⁶-isothiazolidin-2-yl)-1H-indazol-3-yl]-2-(2-methylphenyl)acetamide, 69. N-[5-(1,1-dioxo-1λ⁶-isothiazolidin-2-yl)-1H-indazol-3-yl]-2-[3-(ethylamino)phenyl]acetamide, 70. 2-[3-(diethylamino)phenyl]-N-[5-(1,1-dioxo-1λ⁶-isothiazolidin-2-yl)-1H-indazol-3-yl]acetamide, 71. 2-(3,5-dimethoxyphenyl)-N-[5-(1,1-dioxo-1λ⁶-isothiazolidin-2-yl)-1H-indazol-3-yl]acetamide, 72. N-[5-(1,1-dioxo-1λ⁶-isothiazolidin-2-yl)-1H-indazol-3-yl]-2-[4-(ethylamino)phenyl]acetamide, 73. 2-[4-(diethylamino)phenyl]-N-[5-(1,1-dioxo-1λ⁶-isothiazolidin-2-yl)-1H-indazol-3-yl]acetamide, 74. 2-(3-chloro-4-ethoxyphenyl)-N-[5-(1,1-dioxo-1λ⁶-isothiazolidin-2-yl)-1H-indazol-3-yl]acetamide, 75. 2-[4-(2-aminoethoxy)phenyl]-N-[5(1,1-dioxo-1λ⁶-isothiazolidin-2-yl)-1H-indazol--3-yl]acetamide, 76. 2-[2-(acetylamino)-1,3-thiazol-4-yl]-N-[5-(1,1-dioxo-1λ⁶-isothiazolidin-2-yl)-1H-indazol-3-yl]acetamide, 77. 2-(2-[4-(benzyloxy)benzyl]amino-1,3-thiazol-4-yl)-N-[5-(1,1-dioxo-1λ⁶-isothiazolidin-2-yl)-1H-indazol-3-yl]acetamide, 78. N-[5-(1,1-dioxo-1λ⁶-isothiazolidin-2-yl)-1H-indazol-3-yl]-2-(3-ethoxyphenyl)acetamide, 79. N-[5-(1,1-dioxo-1λ⁶-isothiazolidin-2-yl)-1H-indazol-3-yl]-2-[4-ethoxy-3-(4-morpholinylsulfonyl)phenyl]acetamide, 80. 2-[3-(aminosulfonyl)-4-ethoxyphenyl]-N-[5-(1,1-dioxo-1λ⁶-isothiazolidin-2-yl)-1H-indazol-3-yl]acetamide, 81. N-[5-(1,1-dioxo-1λ⁶-isothiazolidin-2-yl)-1H-indazol-3-yl]-2-4-ethoxy-3-[(4-methyl-1-piperazinyl)sulfonyl]phenylacetamide, and 82. 2-[4-(2-aminoethoxy)phenyl]-N-[5-(1,1-dioxo-1λ⁶-isothiazolidin-2-yl)-1H-indazol-3-yl]acetamide.

4. A composition of anti-cancer agent comprising the compound of formula (1), or pharmaceutically acceptable salt, solvated product or isomer thereof as defined in claim 1 as an active ingredient together with a pharmaceutically acceptable carrier.

5. A process for preparing the compound of formula (1), or pharmaceutically acceptable salt, solvated product or isomer thereof as defined in claim 1 which comprises a) reacting anthralilonitrile with hydroxylamine to produce an amidoxime of the following formula (2):

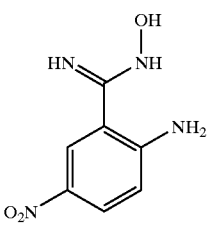

b) reacting the amidoxime with ester to produce a 3-aminoindazole of the following formula (3):

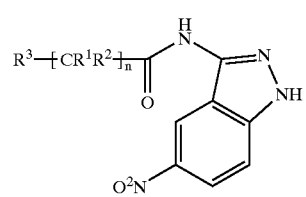

wherein R¹, R², R³ and n are as defined in claim 1, c) protecting the 1-position of 3-aminoindazole by t-butylcarbamate to produce a compound of the following formula (4):

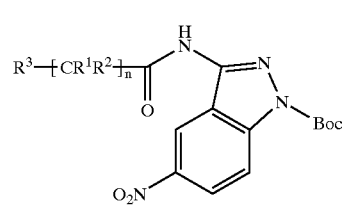

wherein R¹, R², R³ and n are as previously described, and Boc represents t-butoxycarbonyl.

d) reducing the nitro group at 5-C of formula (4) to produce an amine of the following formula (5):

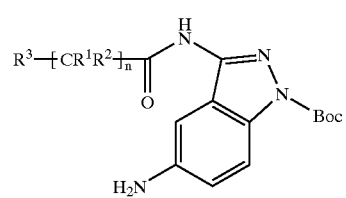

wherein, R¹, R², R³ and n are as previously described, and Boc represents t-butoxycarbonyl.

e) reacting the amine of formula (5) with sulfonyl chloride to produce a sulfonamide of the following formula (6):

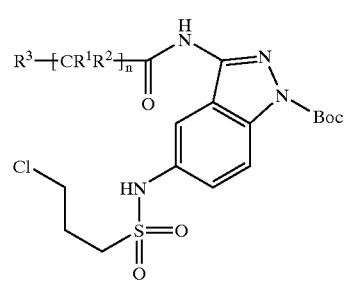

wherein, $R^1$, $R^2$, $R^3$ and n are as previously described, and Boc represents t-butoxycarbonyl.

e) cyclizing the compound of formula (6) through intramolecular ring-closing to synthesize a dioxoisothiazolidine of the following formula (7):

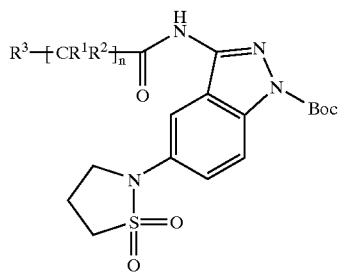

(7)

wherein $R^1$, $R^2$, $R^3$ and n are as previously described, and Boc represents t-butoxycarbonyl, and f) deprotecting the compound of formula (7).

6. The process for preparing the compound of formula (1), or pharmaceutically acceptable salt, solvated product or isomer thereof according to claim 5 which comprises a) reacting a compound of formula (1) wherein X is oxygen atom with Lawesson's reagent to produce a compound of formula (1) wherein X is sulfur atom; or b) reacting the compound of formula (1) wherein X is sulfur atom with a compound of the following formula (8):

 (8)

wherein $R^4$ is as defined in claim 1, to produce a compound of formula (1) wherein X is nitrogen atom.

7. A process for preparing the compound of formula (1), or pharmaceutically acceptable salt, solvated product or isomer thereof which compises reacting an indazole intermediate of the following formula (9):

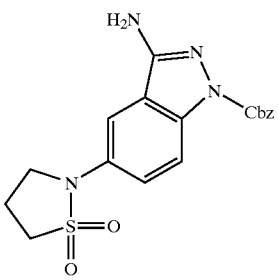

(9)

wherein Cbz represents benzyloxycarbonyl, with an acylhalide of the following formula (10):

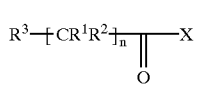

(10)

wherein $R^1$, R2, $R^3$ and n are as defined in claim 1, and X' represents halogen.

8. A compound of formula (9):

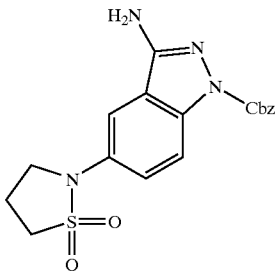

(9)

wherein Cbz represents benzyloxycarbonyl, as an intermediate for preparing the compound of formula (1), or pharmaceutically acceptable salt, solvated product or isomer thereof as defined in claim 1.

* * * * *